(12) United States Patent  
Guo et al.

(10) Patent No.: US 8,119,800 B2  
(45) Date of Patent: Feb. 21, 2012

(54) PROCESSES FOR PREPARING HIV REVERSE TRANSCRIPTASE INHIBITORS

(75) Inventors: Hongyan Guo, San Mateo, CA (US); Stacey Heumann, Redwood City, CA (US); Ill Young Lee, Daejeon (KR); Michael L. Mitchell, Hayward, CA (US); Steven Pfeiffer, Pleasanton, CA (US); Jong Chan Son, Daejeon (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 556 days.

(21) Appl. No.: 12/336,762

(22) Filed: Dec. 17, 2008

(65) Prior Publication Data

US 2009/0163712 A1    Jun. 25, 2009

Related U.S. Application Data

(60) Provisional application No. 61/016,194, filed on Dec. 21, 2007.

(51) Int. Cl.  
C07D 239/02    (2006.01)

(52) U.S. Cl. .................. 544/312; 544/243; 544/311

(58) Field of Classification Search .................. 544/243, 544/311, 312  
See application file for complete search history.

(56) References Cited

U.S. PATENT DOCUMENTS

| | | |
|---|---|---|
| 4,518,685 A | 5/1985 | Yagihara et al. |
| 4,656,209 A | 4/1987 | Wehner et al. |
| 5,112,835 A | 5/1992 | Miyasaka et al. |
| 5,162,326 A | 11/1992 | Naka et al. |
| 5,188,928 A | 2/1993 | Karino et al. |
| 5,219,869 A | 6/1993 | Shiokawa et al. |
| 5,227,284 A | 7/1993 | Matushita et al. |
| 5,266,453 A | 11/1993 | Matushita et al. |
| 5,318,972 A | 6/1994 | Miyasaka et al. |
| 5,461,060 A | 10/1995 | Miyasaka et al. |
| 5,604,209 A | 2/1997 | Ubasawa et al. |
| 5,643,744 A | 7/1997 | Nitta et al. |
| 5,747,500 A | 5/1998 | Son et al. |
| 5,859,100 A | 1/1999 | Wehner et al. |
| 5,889,013 A | 3/1999 | Kim et al. |
| 5,922,727 A | 7/1999 | Cho et al. |
| 5,998,411 A | 12/1999 | Vig et al. |
| 6,136,815 A | 10/2000 | Son et al. |
| 6,174,941 B1 | 1/2001 | Wehner et al. |
| 6,174,998 B1 | 1/2001 | Muhlegger et al. |
| 6,177,437 B1 | 1/2001 | Wright |
| 6,372,725 B1 | 4/2002 | Zilch et al. |
| 6,713,486 B1 | 3/2004 | Son et al. |
| 6,911,450 B1 | 6/2005 | Tronchet |
| 6,987,114 B1 | 1/2006 | Cho et al. |
| 7,250,421 B2 | 7/2007 | Nair et al. |
| 2003/0114445 A1* | 6/2003 | Zhi et al. .................. 514/227.8 |
| 2005/0215568 A1 | 9/2005 | Howell et al. |
| 2006/0223834 A1 | 10/2006 | Nair et al. |

FOREIGN PATENT DOCUMENTS

| | | |
|---|---|---|
| CN | 101016265 A | 8/2007 |
| EP | 929533 A1 | 7/1999 |
| EP | 929533 B1 | 7/1999 |
| FR | 2779721 A1 | 12/1999 |
| FR | 2779722 A1 | 12/1999 |
| JP | 3264579 A | 11/1991 |
| JP | 05289238 A | 11/1993 |
| JP | 06135943 A | 5/1994 |
| JP | 08003143 A | 1/1996 |
| JP | 09020792 A | 1/1997 |
| JP | 10130244 A | 5/1998 |
| JP | 10168068 A | 6/1998 |
| JP | 11102047 A | 4/1999 |
| JP | 2001114767 A | 4/2001 |
| JP | 2002284686 | 10/2002 |
| JP | 2005/212143 A | 8/2005 |
| MX | 2003PA11298 | 6/2005 |
| WO | WO-89/10701 A1 | 11/1989 |
| WO | WO-92/00964 A1 | 1/1992 |
| WO | WO-93/02044 A1 | 2/1993 |
| WO | WO-93/16091 A1 | 8/1993 |
| WO | WO-93/16092 A1 | 8/1993 |
| WO | WO-98/33505 A1 | 8/1998 |

(Continued)

OTHER PUBLICATIONS

Y. He et al., Monatshefte fur Chemie, 136, 1233-1245 (2005).*

(Continued)

*Primary Examiner* — James O Wilson  
*Assistant Examiner* — Alexander R Pagano  
(74) *Attorney, Agent, or Firm* — Edwards Wildman Palmer LLP

(57) ABSTRACT

Compounds of Formula (I):

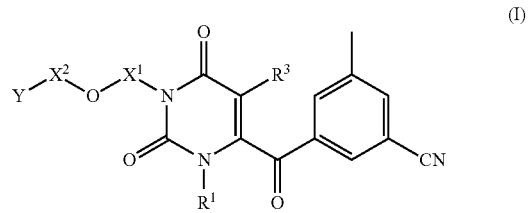

can be prepared by a multi-step process from compounds of Formula (II):

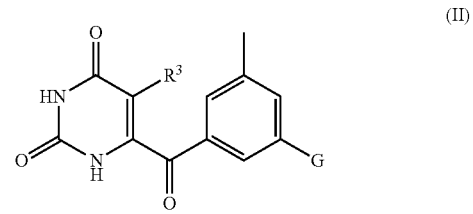

wherein G is Cl, Br or I.

23 Claims, No Drawings

FOREIGN PATENT DOCUMENTS

| | | | |
|---|---|---|---|
| WO | WO-00/51990 | A1 | 9/2000 |
| WO | WO 0051990 | A1 * | 9/2000 |
| WO | WO-00/61563 | A1 | 10/2000 |
| WO | WO-00/61564 | A2 | 10/2000 |
| WO | WO 0061564 | A1 * | 10/2000 |
| WO | WO 0071523 | A1 * | 11/2000 |
| WO | WO-01/23363 | A1 | 4/2001 |
| WO | WO-01/79203 | | 10/2001 |
| WO | WO 01/83459 | A2 | 11/2001 |
| WO | WO-03/029226 | A1 | 4/2003 |
| WO | WO-03/057677 | A1 | 7/2003 |
| WO | WO-03/064511 | A2 | 8/2003 |
| WO | WO-03/091264 | A2 | 11/2003 |
| WO | WO 2005009973 | A1 * | 2/2005 |
| WO | WO-2005/026184 | A2 | 3/2005 |
| WO | 2005/120577 | A2 | 12/2005 |
| WO | WO-2005/120577 | A2 | 12/2005 |
| WO | WO 2005120577 | A2 * | 12/2005 |
| WO | WO-2006/070292 | A2 | 7/2006 |
| WO | WO-2006/089221 | A2 | 8/2006 |
| WO | WO-2007/091857 | A1 | 8/2007 |
| WO | WO-2007/104834 | A1 | 9/2007 |
| WO | WO-2007/106450 | A2 | 9/2007 |
| WO | WO-2008/016522 | A2 | 2/2008 |
| WO | WO 2008016522 | A2 * | 2/2008 |
| WO | 2009/005674 | A2 | 1/2009 |
| WO | 2009/005693 | A1 | 1/2009 |
| WO | WO-2009/005674 | A2 | 1/2009 |
| WO | WO-2009/005693 | A1 | 1/2009 |
| WO | WO 2009005674 | A2 * | 1/2009 |
| WO | WO 2009005693 | A1 * | 1/2009 |

OTHER PUBLICATIONS

A. El-Emam et al., Bull. Korean Chem. Soc. 25(7), 991 (2004).*

M. Hatsuda et al., Tetrahedron Lett. (46) 1849-1853 (2005).*

D. Goldstein et al., J. Med. Chem. 49(5), 1562-1575 (2006).*

Littke et al. (2007) "Mild and General Methods for the Palladium-Catalyzed Cyanation of Aryl and Heteroaryl Chlorides," *Organic Letters* 9(9)1711-1714.

Romines, Karen et al. 2006 "Structure-Activity Relationship Studies of Novel Benzophenones Leading to the Discovery of a Potent, Next Generation HIV Nonnucleoside Reverse Transcriptase Inhibitor," *Journal of Medicinal Chemistry, American Chemical Society* 49(2):727-739.

Sundermeier et at. (2003) "Palladium-Catalyzed Cyanation of Aryl HalidesL Recent Developments and Perspectives," *Eur, J. Inorg. Chem* 3513-3526.

Zhu et al. (2007) "Pd/C: A Recyclable Catalyst for Cyanation of Aryl Bromides," *Eur. J. Org. Chem.* 2401-2404.

International Search Report issued in International Application No. PCT/US2008/087106; Date of Mailing: Jul. 1, 2010.

Journal of Medicianal Chemistry; American Chemical Society. Washington.; US, vol. 49, No. 2, Jan. 26, 2006, pp. 727-739, XP008089364 ISSN: 0022-2623.

\* cited by examiner

PROCESSES FOR PREPARING HIV REVERSE TRANSCRIPTASE INHIBITORS

This application is filed under 35 U.S.C. 111(a) claiming the benefit under 35 U.S.C. 119(e) to provisional application 61/016,194 filed Dec. 21, 2007 which is herein incorporated by reference in its entirety.

FIELD OF THE INVENTION

This invention relates to processes and novel intermediate compounds for preparing HIV reverse transcriptase (RT) inhibitors.

BACKGROUND OF THE INVENTION

In recent years, inhibitors of HIV reverse transcriptase (RT) have become an important class of therapeutic agents for inhibition and treatment of HIV infection in humans. Compounds that inhibit the enzymatic functions of HIV reverse transcriptase inhibit replication of HIV in infected cells. Such compounds are useful in the prevention or treatment of HIV infection in humans, as demonstrated by known RT inhibitors such as zidovudine, didanosine, zalcitabine, stavudine, lamivudine, emtricitabine, abacavir, tenofovir, nevirapine, delavirdine and efavirenz, the main drugs thus far approved for use in the treatment of AIDS. More recently, Guo, et al., described aroylpyrimidine RT inhibitors in WO2008016522 which is incorporated herein by reference in its entirety.

As with any antiviral therapy, use of RT inhibitors in the treatment of AIDS eventually leads to a virus that is less sensitive to the given drug. Resistance (reduced sensitivity) to these drugs is the result of mutations that occur in the reverse transcriptase segment of the pol gene. Several mutant strains of HIV have been characterized and resistance to known therapeutic agents is believed to be due to mutations in the RT gene. Thus, to be effective, new HIV RT inhibitors must be effective not only against wild-type strains of HIV, but must also demonstrate efficacy against the newly emerging mutant strains that are resistant to the commercially available RT inhibitors. Accordingly, there continues to be a need for new HIV RT inhibitors, and improved methods for preparing new HIV RT inhibitors.

SUMMARY OF THE INVENTION

The present invention is directed to a method of preparing HIV RT inhibitor compounds of Formula (I):

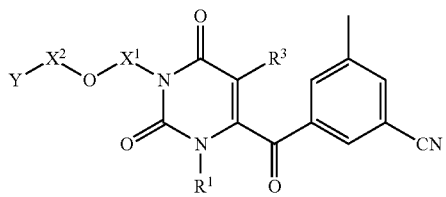

or pharmaceutically acceptable tautomers, salts, solvates, and/or esters thereof wherein:
$R^1$ and $R^3$ are each independently H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, or substituted heterocyclyl, arylalkyl, substituted arylalkyl, heteroarylalkyl; or substituted heteroarylalkyl;

$X^1$ is allylene, substituted alkylene, alkenylene, substituted alkenylene, alkynylene, substituted alkynylene, carbocyclylene, substituted carbocyclylene, heterocyclylene, or substituted heterocyclylene;

$X^2$ is a covalent bond, alkylene, or substituted alkylene;

Y is selected from a group consisting of:

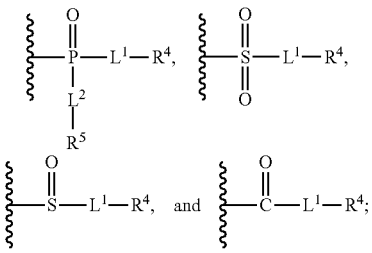

$L^1$ and $L^2$ are each independently a covalent bond, —O—, or —$NR^6$—;

$R^4$ and $R^5$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—$R^7$, -(substituted alkylene)-C(O)—O—$R^7$, -alkylene-O—C(O)—O—$R^7$, or -(substituted alkylene)-O—C(O)—O—$R^7$; and $R^6$ and $R^7$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl;

said method comprising:
(d) reacting a compound of Formula (II) wherein G is Cl, Br, or I with a cyanide reagent:

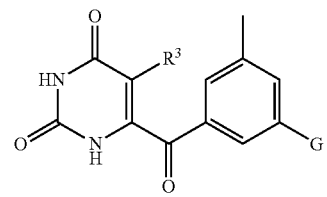

thereby forming a compound of Formula (III):

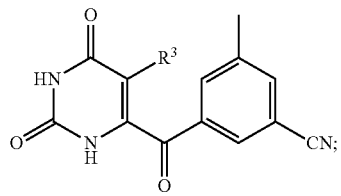

(e) reacting the compound of Formula (III) with $R^1Z^1$, wherein $Z^1$ is a leaving group, thereby forming a compound of Formula (IV):

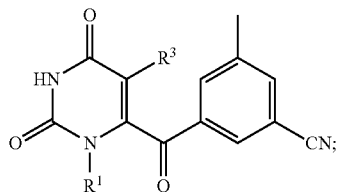

(f) reacting the compound of Formula (IV) with Y—$X^2$—O—$X^1$—$Z^2$, wherein $Z^2$ is a leaving group, thereby forming the compound of Formula (I).

DETAILED DESCRIPTION

Reference will now be made in detail to certain embodiments of the invention, examples of which are illustrated in the accompanying structures, formulae, and reaction schemes. While the invention will be described in conjunction with the embodiments, it will be understood that they are not intended to limit the invention to those embodiments. On the contrary, the invention is intended to cover all alternatives, modifications, and equivalents, which may be included within the scope of the present invention as defined by the claims.

Unless stated otherwise, the following terms and phrases as used herein are intended to have the following meanings:

When trade names are used herein, applicants intend to independently include the tradename product and the active pharmaceutical ingredient(s) of the tradename product.

In accordance with a convention used in the art,

is used in structural formulas herein to depict the bond that is the point of attachment of the moiety or substituent to the core or backbone structure.

As used herein, "a compound of the invention" or "a compound of Formula (I)-Formula (VIII)" means a compound of Formula (I)-Formula (VIII) or a pharmaceutically acceptable salt, solvate, stereoisomer or physiologically functional derivative thereof. Similarly, with respect to isolatable intermediates such as for example, compounds of formula (4), the phrase "a compound of formula (number)" means a compound of that formula and pharmaceutically acceptable salts, solvates stereoisomers and physiologically functional derivatives thereof.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 10 carbon atoms (i.e., $C_1$-$C_{10}$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2C_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkyne), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—$CH(CH_3)$—), 1,2-ethyl (—$CH_2CH_2$—), 1,1-propyl (—$CH(CH_2CH_3)$—), 1,2-propyl (—$CH_2CH(CH_3)$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡CH—).

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or Sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or Sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

The term "substituted" in reference to alkyl, alkylene, aryl, arylalkyl, heterocyclyl, etc., for example, "substituted alkyl", "substituted alkylene", "substituted aryl", "substituted arylalkyl", "substituted heterocyclyl", and "substituted carbocyclyl" means alkyl, alkylene, aryl arylalkyl, heterocyclyl, carbocyclyl respectively, in which one or more hydrogen atoms are each independently replaced with a non-hydrogen substituent. Typical substituents include, but are not limited to, —X, —R, —O$^-$, =O, —OR, —SR, —S$^-$, —NR$_2$, —N$^+$R$_3$, =NR, —CX$_3$, —CN, —OCN, —SCN, —N=C=O, —NCS, —NO, —NO$_2$, =N$_2$, —N$_3$, —NHC(=O)R, —C(=O)R, —C(=O)NRR—S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —N(=O)(OR)$_2$, —N(=O)(O$^-$)$_2$, —N(=O)(OH)$_2$, —N(O)(OR)(O$^-$), —C(=O)R, —C(=O) X, —C(S)R, —C(O)OR, —O—C(O)R, —C(O)O$^-$, —C(S) OR, —C(O)SR, —C(S)SR, —C(O)NRR, —C(S)NRR, —C(=NR)NRR, where each X is independently a halogen: F, Cl, Br, or I; and each R is independently H, alkyl, aryl, arylalkyl, a heterocycle, or a protecting group or prodrug moiety, Alkylene, alkenylene, and alkynylene groups may also be similarly substituted.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds disclosed herein should be selected in order to provide a compound which is sufficiently stable to provide a pharmaceutically useful compound which can be formulated into an acceptably stable pharmaceutical composition. Compounds which have such stability are contemplated as falling within the scope of the present invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl, and the like.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclene" refers to a heterocycle as defined herein having two monovalent radical centers derived by the removal of two hydrogen atoms from the same carbon atom or two different carbon or nitrogen atoms of a parent heterocycle.

"Heterocyclylalkyl" refers to an acyclic alkyl radical in which one of the hydrogen atoms bonded to a carbon atom, typically a terminal or $sp^3$ carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 6 to 20 carbon atoms, e.g., the alkyl portion of the arylalkyl group is 1 to 6 carbon atoms and the heterocyclyl moiety is 5 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 6 to 20 carbon atoms, e.g., the alkenyl portion of the heterocyclyl alkenyl group is 1 to 6 carbon atoms and the heterocyclyl moiety is 5 to 14 carbon atoms.

"Heterocyclylalkynyl" refers to an acyclic alkynyl radical in which one of the hydrogen atoms bonded to a carbon atom, typically a terminal or $Sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 6 to 20 carbon atoms, e.g., the alkynyl portion of the heterocyclyl alkynyl group is 1 to 6 carbon atoms and the heterocyclyl moiety is 5 to 1.4 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl.

"Carbocyclene" refers to a saturated (i.e., cycloalkyl), partially unsaturated (e.g., cycloakenyl, cycloalkadienyl, etc.) or aromatic radical as described for "carbocycle" having two monovalent radical centers derived by the removal of two hydrogen atoms from the same or two different carbon atoms of a parent carbocycle.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. in addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, $CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

The terms "phosphonate" and "phosphonate group" mean a functional group or moiety within a molecule that comprises at least one phosphorus-carbon bond, and at least one phosphorus-oxygen double bond. The phosphorus atom is further substituted with oxygen, sulfur, and nitrogen substituents. As defined herein, "phosphonate" and "phosphonate group" include molecules with phosphonic acid, phosphonic monoester, phosphonic diester, phosphonamidate, phosphondiamidate and phosphonthioate functional groups.

"Linker" or "link" refers to a chemical moiety comprising a covalent bond or a chain or group of atoms that covalently attaches a phosphonate or phosphinate group to a drug. Linkers which include moieties such as: repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide.

"Optionally substituted" refers to a particular moiety of the compound of Formula (I) (e.g., an optionally substituted aryl group) refers to a moiety having 0, 1, 2, or more substituents.

"Ester thereof" means any ester of a compound in which any of the —COOH functional groups of the molecule is replaced by a —COOR function, or any of the —OH functional groups of the molecule is replaced with a —O—C(O)R in which the R moiety of the ester is any carbon-containing group which forms a stable ester moiety, including but not limited to alkyl alkenyl, alkynyl, cycloalkyl, cycloalkylalkyl, aryl, arylalkyl, heterocyclyl, heterocyclylalkyl and substituted derivatives thereof. The term "ester thereof" includes but is not limited to pharmaceutically acceptable esters thereof.

"Salt thereof" means any acid and/or base addition salt of a compound according to the invention; preferably a pharmaceutically acceptable salt thereof.

"Pharmaceutically acceptable salt" means a salt of a compound which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. Where applicable and compatible with the chemical properties of the compound of formula (I), (II), (III), the term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19.

"Chiral" refers to molecules which have the property of non-superimposability of the mirror image partner, while the term "achiral" refers to molecules which are superimposable on their mirror image partner.

"Stereoisomers" refers to compounds which have identical chemical constitution, but differ with regard to the arrangement of the atoms or groups in space. Stereoisomers include, e.g. diastereomers and enantiomers as described herein.

"Diastereomer" refers to a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. N. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The modifier "about" used in connection with a quantity is inclusive of the stated value and has the meaning dictated by the context (e.g., includes the degree of error associated with measurement of the particular quantity).

The term "transition metal" refers to groups 3-12 of the periodic table. This would expressly include zinc, cadmium and mercury.

Protecting Groups

In the context of the present invention, protecting groups include prodrug moieties and chemical protecting groups.

Protecting groups are available, commonly known and used, and are optionally used to prevent side reactions with the protected group during synthetic procedures, i.e. routes or methods to prepare the compounds of the invention. For the most part the decision as to which groups to protect, when to do so, and the nature of the chemical protecting group "PG" will be dependent upon the chemistry of the reaction to be protected against (e.g., acidic, basic, oxidative, reductive or other conditions) and the intended direction of the synthesis. The PG groups do not need to be, and generally are not, the same if the compound is substituted with multiple PG. In general, PG will be used to protect functional groups such as carboxyl, hydroxyl, thio, or amino groups and to thus prevent side reactions or to otherwise facilitate the synthetic efficiency. The order of deprotection to yield free, deprotected groups is dependent upon the intended direction of the synthesis and the reaction conditions to be encountered, and may occur in any order as determined by the artisan.

Various functional groups of the compounds of the invention may be protected. For example, protecting groups for —OH groups (whether hydroxyl, carboxylic acid, phosphonic acid, or other functions) include "ether- or ester-forming groups". Ether- or ester-forming groups are capable of functioning as chemical protecting groups in the synthetic schemes set forth herein. However, some hydroxyl and thio protecting groups are neither ether- nor ester-forming groups, as will be understood by those skilled in the art, and are included with amides, discussed below.

A very large number of hydroxyl protecting groups and amide-forming groups and corresponding chemical cleavage reactions are described in *Protective Groups in Organic Synthesis*, Theodora W. Greene and Peter G. M. Wuts (John Wiley & Sons, Inc., New York, 1999, ISBN 0-471-16019-9) ("Greene"). See also Kocienski, Philip J.; *Protecting Groups* (Georg Thieme Verlag Stuttgart, New York, 1994), both of which are herein incorporated by reference in their entirety for all purposes. In particular Chapter 1, Protecting Groups: An Overview, pages 1-20, Chapter 2, Hydroxyl Protecting Groups, pages 21-94, Chapter 3, Diol Protecting Groups, pages 95-117, Chapter 4, Carboxyl Protecting Groups, pages 118-154, Chapter 5, Carbonyl Protecting Groups, pages 1.55-184. For protecting groups for carboxylic acid, phosphonic acid, phosphonate, sulfonic acid and other protecting groups for acids see Greene as set forth below. Such groups include by way of example and not limitation, esters, amides, hydrazides, and the like.

Ether- and Ester-Forming Protecting Groups

Ester-forming groups include: (1) phosphonate ester-forming groups, such as phosphonamidate esters, phosphorothioate esters, phosphonate esters, and phosphon-bis-amidates; (2) carboxyl ester-forming groups, and (3) sulphur esters forming groups, such as sulphonate, sulfate, and sulfinate.

One skilled in the art will recognize that the pyrimidinedione rings of the compounds of Formula (I)-(IV) can exist in tautomeric forms. For example, but not by way of limitation, structures (a) and (b) can have equivalent tautomeric forms as shown below:

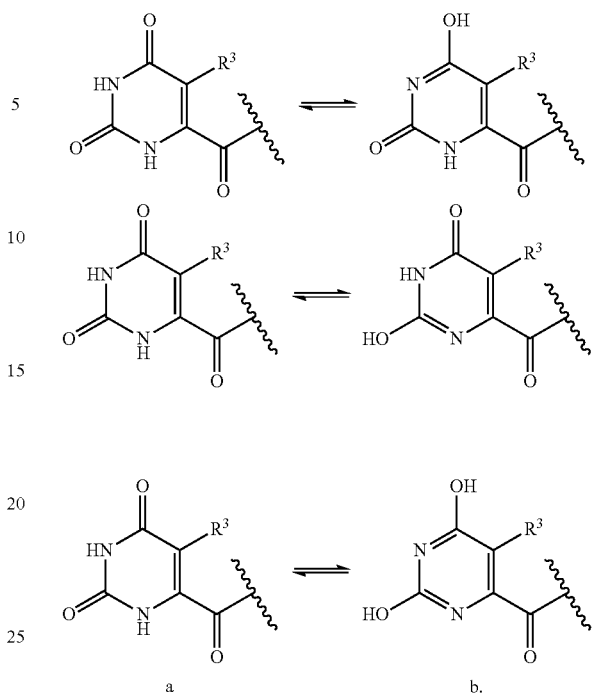

a.  b.

All possible tautomeric forms of the pyrimidinediones of all of the embodiments are within the scope of the invention.

In its many embodiments, the present invention is directed to methods for preparing compounds of Formula (I):

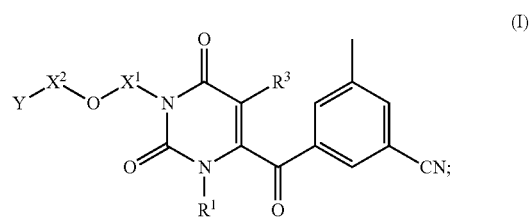

(I)

wherein $R^1$ and $R^3$ are each independently H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, or substituted heterocyclyl, arylalkyl, substituted arylalkyl, heteroarylalkyl; or substituted heteroarylalkyl. In a particular embodiment, $R^1$ and $R^3$ are each independently alkyl groups. In another particular embodiment, $R^3$ is isopropyl. In yet another embodiment, $R^1$ is ethyl. In still another embodiment, $R^1$ is ethyl and $R^3$ is isopropyl.

The compounds of Formula (I) are HIV RT inhibitors.

The group —$X^1$—O—$X^2$—Y includes alkylene esters of phosphonic, sulfonic, sulfinic, and carboxylic acids, wherein $X^1$ is alkylene, substituted alkylene, alkenylene, substituted alkenylene, alkynylene, substituted alkynylene, carbocyclylene, substituted carbocyclylene, heterocyclylene, or substituted heterocyclylene; $X^2$ is a covalent bond, alkylene, or substituted alkylene; and Y is:

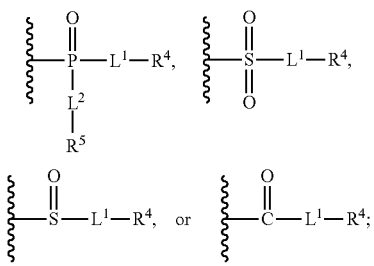

$L^1$ and $L^2$ are each independently a covalent bond, —O—, or —$NR^6$—; $R^4$ and $R^5$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—$R^7$, -(substituted alkylene)-C(O)—O—$R^7$, -alkylene-O—C(O)—O—$R^7$, or -(substituted alkylene)-O—C(O)—O—$R^7$; and $R^6$ and $R^7$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl. In one embodiment, $X^1$ is —$CH_2$—. In another embodiment, $X^2$ is a covalent bond. In yet another embodiment, —$X^1$—O—$X^2$—Y is —$CH_2$—O—Y. In still another embodiment, Y is

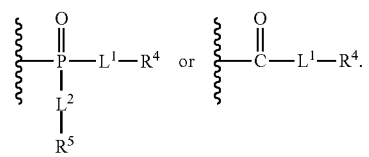

In still yet another embodiment, Y is $P(O)(OH)_2$ or —C(O)-alkyl. In yet still another embodiment, Y is —$P(O)(OH)_2$ or —C(O)—$CH_3$. In another embodiment, —$X^1$—O—$X^2$—Y is —$CH_2$—O—C(O)—$R^4$. In a particular embodiment, —$X^1$—O—$X^2$—Y is —$CH_2$—O—C(O)—$CH_3$.

Compounds of Formula (I) can be prepared in several steps from a compound of Formula (II):

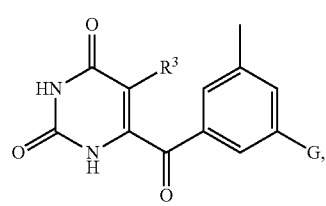

wherein G is Cl, Br, or I, by treating a compound of Formula (II) with a cyanide reagent comprising a source of cyanide ion; e.g., a metal, tetraalkylammonium, or organic cyanide or organic thiocyanates; and a transition metal catalyst, thereby forming:

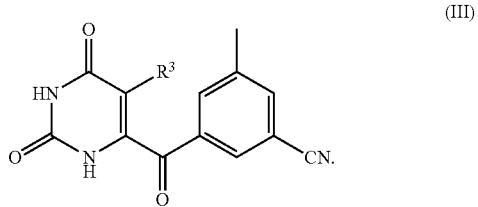

Non-limiting examples of cyanide ion sources include alkali metal cyanides, alkaline earth cyanides, transition metal cyanides, CuCN, $Zn(CN)_2$, potassium hexacyanoferrate, trialkylsilylcyanide, acetone cyanohydrin, and benzylthiocyanate. In a preferred embodiment the cyanide ion source is $Zn(CN)_2$. Typically, the mole ratio of a compound of Formula (II) to cyanide ion is from about 1:1 to about 1:4; preferably a ratio of about 1:1 to about 1:1.5. The amount of transition metal catalyst used is typically about 0.01 to about 5 mole percent of the compound of Formula (II), more typically about 0.01 to about 2 mole percent. The preparation is typically run in an inert solvent, preferably, but not limited to, an anhydrous polar solvent such as DMF, DMA, NMP, THF or dioxane. The reaction is typically heated at about 60 to about 160° C. for about one to about 24 hours. Preferably, the reaction is heated to about 100 to about 120° C. for about one to about three hours.

In another aspect, the cyanide reagent comprises a palladium(0) or palladium(II) catalyst (e.g., Tsuji, J., *Palladium Reagents and Catalyst: New Perspectives for the 21st Century*, John Wiley & Sons, 2004, ISBN 0-470-85033-7; Sundermeier, M., *Eur. J. Inorg. Chem.* 2003, 3513-3526). Non-limiting examples of these palladium catalysts are $Pd_2dba_3$, $Pd(dba)_2$, $PdBr_2$, $PdCl_2$, $Pd(acetate)_2$, $Pd(trifluoroacetate)_2$, $Pd(triphenylphosphine)_4$, $PdCl_2(triphenylphosphine)_2$, $Pd(tri-tert-butylphosphine)_2$ and Pd on carbon. Some of these palladium catalyst show improved activity when combined with a phosphine-containing ligand. Non-limiting examples of phosphine-containing ligands are 1,1'-bis(diphenylphosphino)ferrocene (DPPF), di-(1-admamantyl)-1-butylphosphine, 2-di-tert-butylphosphino-1,1'-binaphthyl, 2-(dicyclohexylphosphino)-2',6'-dimethoxy-1,1'-biphenyl (S-Phos), 2-(dicyclohexylphosphino)-2',4',6'-tri-iso-propyl-1,1'-biphenyl (X-Phos), 1,5-bis(diphenylphosphino)pentane, tri(cyclohexyl)phosphine, triphenylphosphine and tri(butyl)phosphine. The preferred mole ratio of phosphine-containing ligand to palladium catalyst is about 4:1 to about 2:1, more preferably about 2:1. Some of these palladium catalysts show improved activity when combined with a co-catalyst such as metallic Zn (Littke, A., *Org. Lett.* 2007, 1711-1714). Some of these palladium catalysts show improved activity with organic base or inorganic base additives (Zhu, Y-Z, *Eur. J. Org. Chem.* 2007, 2401-2404). Non-limiting examples of organic base additives are tributylamine, triethylamine, N,N, N',N'-tetramethylethylenediamine, and 1,4-diazabicyclo[2.2.2]octane. Non-limiting examples of inorganic bases additives are sodium carbonate and potassium carbonate. In a preferred embodiment of this aspect, the amount of palladium (0) or palladium(II) catalyst used is about 0.01 to about 5 mole percent of the compound of Formula (II), more preferably about 0.01 to 1.5 mole percent, most preferably less than about 1 mole percent. In a preferred embodiment of this aspect, the cyanide reagent also comprises $Zn(CN)_2$. In a particularly preferred embodiment the cyanide reagent comprises a combination of $Zn(CN)_2$, DPPF (1,1'-bis(diphenylphosphino)ferrocene) and $Pd_2dba_3$. In another particularly preferred embodiment the cyanide reagent comprises a combination of $Zn(CN)_2$, DPPF and $Pd_2dba_3$ wherein the amount of $Pd_2dba_3$ is less than about 1.1 mole percent of the compound of Formula (II). In another preferred embodiment the compound of Formula (III) is obtained in greater than about 80% yield.

The compound of Formula (III) can then be alkylated, alkenylated, alkynylated, arylated, etc. with a compound of formula $R^1Z^1$, wherein $R^1$ is as defined herein, and $Z^1$ is an appropriate leaving group (i.e., an atom or group of atoms that "detaches" from $R^1$, e.g., in an $S_N1$ or $S_N2$ reaction mechanism) which permits attachment of $R^1$ to the nitrogen in the 3-position of the tetrahydropyrimidine ring. Non-limiting examples of leaving groups are halides (chloro, bromo, and iodo), alkyl and aryl sulfonates, triflates, alkyl carbonates, fluorosulfonates, and alkylsulfates. The resulting compound has the Formula (IV):

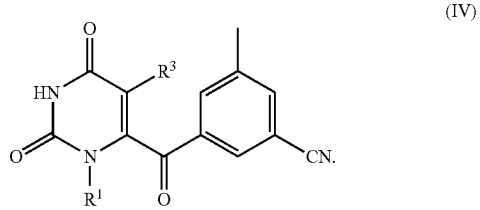

(IV)

The mole ratio of $R^1Z^1$ to the compound of Formula (III) is typically about 1:1 to about 1:4, preferably about 1:1 to about 1:1.3. In some embodiments, the reaction is run in an inert solvent, preferably, but not limited to, an anhydrous polar solvent such as DMF, DMA or dioxane. In some embodiments, the reaction is run at a temperature of about 0 to about 80° C. in presence of an organic or inorganic base for about one to about 24 hours. Non-limiting examples of inorganic bases are sodium carbonate and potassium carbonate. Non-limiting examples of organic bases are triethylamine, di-isopropylethylamine and DMAP. In one embodiment, $R^1Z^1$ is an alkyl halide, for example an alkyl bromide or alkyl iodide. In a particular embodiment, $R^1Z^1$ is ethyl iodide or ethyl bromide. In some embodiments, the compound of Formula (III) is alkylated with ethyl iodide in the presence of an acid acceptor such as an alkali metal or alkaline earth carbonate such as $Na_2CO_3$ or $K_2CO_3$. In another embodiment, the compound of Formula (III) is alkylated with ethyl iodide in the presence of $K_2CO_3$ at ambient temperature wherein the mole ratio of the compound of Formula (III) to ethyl iodide is about 1:1.3.

In another aspect of the instant invention, the compound of Formula (IV) is prepared from a compound of Formula (II) without the isolation of intermediate compound (III). Typically, the compound of Formula (II) is treated with a cyanide reagent as defined herein wherein the mole ratio of Formula (II) to cyanide ion is about 1:1 to 1:1.3 and the amount of transition metal catalyst is about 0.01 to 1.5 mole percent of the compound of Formula (II). Preferably, the reaction is run in an anhydrous polar solvent such as, but not limited to, DMF at about 100 to about 120° C. for about one to six hours. Typically, the reaction is then cooled to ambient temperature and treated with an alkali metal carbonate such as sodium or potassium carbonate wherein the mole ratio of the compound of Formula (II) to the alkali metal carbonate is about 1:1 to about 1:3, preferably about 1:2.25. The mixture is then treated with a compound of formula $R^1Z^1$ as defined herein wherein the mole ratio of the compound of Formula (II) to the compound of $R^1Z^1$ is about 1:1 to about 1:3, preferably about 1:2.35, for about one to about 24 hours at about 25 to about 100° C., preferably about 60 to 65° C. In a preferred embodiment, $R^1Z^1$ is ethyl iodide. In another preferred embodiment the cyanide reagent comprises a combination of $Zn(CN)_2$, DPPF (1,1'-bis(diphenylphosphino)ferrocene) and $Pd_2dba_3$. In another preferred embodiment, $R^3$ of Formula II is isopropyl and $R^1Z^1$ is ethyl iodide.

The compound of Formula (IV) is then treated with a reagent of formula $Y-X^2-O-X^1-Z^2$ in the presence of a suitable base thereby forming a compound of Formula (I), wherein $Z^2$ is a leaving group (as defined herein). $Y-X^2-O-X^1-$ is as defined herein, and $Z^2$ is an appropriate leaving group (e.g., as described above for $Z^1$) which permits attachment of $Y-X^2-O-X^1-$ to the nitrogen in the 1-position of the tetrahydropyrimidine ring. Non-limiting examples of suitable bases include NaH, $CaH_2$, LiH, butyllithium and alkali metal tert-butoxides. In some embodiments, the reaction is run in an inert solvent, preferably, but not limited to, an anhydrous polar solvent such as DMF, DMA, DMSO or dioxane. In some embodiments, the reaction is conducted from about 0 to about 80° C. for about one to about 24 hours. The mole ratio of the compound of Formula (IV) to the reagent of formula $Y-X^2-O-X^1-Z^2$ is typically about 1:1 to about 1:4; preferably about 1:1 to about 1:1.3. In one embodiment, $Y-X^2-O-X-Z^2$ is $CH_3-C(O)-O-CH_2-Br$, $CH_3-C(O)-O-CH_2-I$, $(HO)_2-P(O)-O-CH_2-Br$, or $(HO)_2-P(O)-O-CH_2-I$. In another preferred embodiment, the reaction is run in DMF at about 0 to about 25° C. using NaH as a base wherein the mole ratio of the compound of Formula (IV) to $CH_3-C(O)-O-CH_2-Br$ is about 1:1 to about 1:1.3.

In another aspect of the instant invention, the compound of Formula (II) is prepared by the hydrolysis of a compound of Formula (VI):

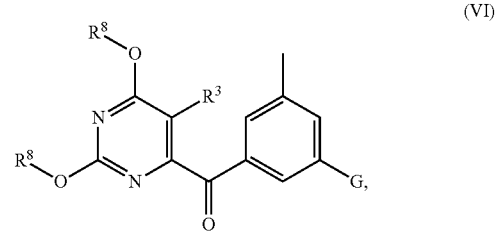

(VI)

wherein G is described herein above and each $R^8$ is a hydroxyl protecting group. For example, each $R^8$ can independently be an alkyl, substituted arylalkyl, a substituted arylalkyl group or a trisubstituted silyl group. In a particular embodiment, $R^8$ is methyl, ethyl, propyl, isopropyl, t-butyl, etc. In another embodiment, $R^8$ is benzyl. In a preferred embodiment, each $R^8$ is methyl. In a particular embodiment, the hydrolysis is carried out in a polar organic solvent such as dioxane or DMF, in the presence of an acid catalyst such as HCl or HBr. Typically, the weight to volume ratio of the compound of Formula (VI) to concentrated HCl or HBr is about 1:1 to about 1:4, preferably about 1:1 to about 1:2.

In another aspect of the instant invention, the compound of Formula (VI) is prepared by the oxidation of a compound of Formula (VII):

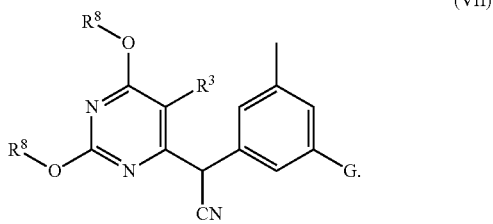

As for the compound of Formula (VII), G is described herein above and each $R^8$ is independently a hydroxyl protecting group as described herein. The CN group in the compound of Formula (VII) is replaced with =O by oxidation to form the compound of Formula (VI), for example by oxidation with $O_2$ in the presence of a suitable base in a polar aprotic solvent. Non-limiting examples of suitable bases are alkali metal hydrides, for example NaH, LiH, or KH, or alkaline earth hydrides, for example $CaH_2$. The mole ratio of the compound of Formula (VII) to suitable base is typically about 1:0.4 to about 1:1.2, more typically about 1:0.45 to about 1:1.1. Non-limiting examples of polar aprotic solvents are DMF, DMA, and NMP. Oxygen is typically bubbled into the reaction for about 1 to about 24 hours.

In another aspect of the instant invention, the compound of Formula (VII) is prepared by treating a compound of Formula (VIII):

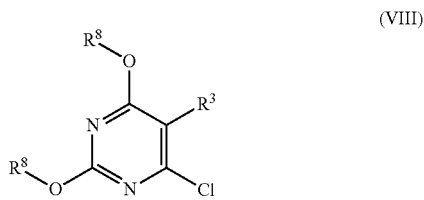

with 3-chloro-5-methylbenzyl cyanide, 3-bromo-5-methylbenzyl cyanide or 3-iodo-5-methylbenzyl cyanide in the presence of a suitable base. $R^8$ in the compound of Formula (VIII) is a hydroxyl protecting group as described herein. Non-limiting examples of suitable bases include NaH, $CaH_2$, LiH, and alkali metal tert-butoxides. Typically the mole ratio of the benzyl cyanide to suitable base is about 1.1.9 to about 1:3, more typically about 1:1.95 to 1:2.2 In some embodiments, the reaction is run in an inert solvent, preferably, but not limited to, an anhydrous polar solvent such as DMF, DMA, DMSO or dioxane. In some embodiments, the reaction is conducted from about 0 to about 80° C. for about one to about 24 hours. The mole ratio of the compound of Formula (VIII) to the 3-chloro-5-methylbenzyl cyanide, 3-bromo-5-methylbenzyl cyanide or 3-iodo-5-methylbenzyl cyanide is typically about 1:1 to about 1.4:1; preferably about 1:1 to about 1.2:1.

In another aspect of the invention, the compound of Formula (II) is prepared from a compound of Formula (VIII) without the isolation of the intermediate compounds of Formula (VII) or Formula (VI). A compound of Formula (VIII) is treated with 3-chloro-5-methylbenzyl cyanide, 3-bromo-5-methylbenzyl cyanide or 3-iodo-5-methylbenzyl cyanide in the presence of a suitable base. Non-limiting examples of suitable bases include NaH, $CaH_2$, and LiH. Typically the mole ratio of the benzyl cyanide to suitable base is about 1:1.9 to about 1:3, more typically about 1:1.95 to 1:2.2. The reaction is run in an inert solvent, preferably, but not limited to, an anhydrous polar solvent such as DMF, DMA, or NMP. In some embodiments, the reaction is conducted from about 0 to about 80° C. for about one to about 24 hours. The mole ratio of the compound of Formula (VIII) to the 3-chloro-5-methylbenzyl cyanide, 3-bromo-5-methylbenzyl cyanide or 3-iodo-5-methylbenzyl cyanide is typically about 1:1 to about 1.4:1; preferably about 1:1 to about 1.2:1. The reaction mixture is then treated with an additional suitable base, typically an alkali metal hydride or alkaline earth hydride such as NaH, LiH or $CaH_2$, followed by bubbling oxygen gas through the mixture. The mole ratio of the compound of starting benzyl cyanide to suitable base is typically about 1:0.45 to about 1:1.1. The oxygen is typically bubbled through the mixture for about 4 to about 24 hours. The reaction is then treated with an acid, typically concentrated HCl or 48% HBr, at about 25 to about 110° C. for about 1 to about 24 hours to give the compound of Formula (II). Typically, the weight to volume ratio of the starting compound of Formula (VIII) to concentrated acid is about 1:2 to about 1:3.

In another aspect of the invention, the concentration of a transition metal impurity in a compound of Formula (I), Formula (III), or Formula (IV) is reduced by treating the reaction mixture, solution, or suspension comprising said compound with a metal chelating agent such as disodium ethylenediaminetetraacetic acid. In another embodiment of this aspect, the reaction mixture, solution, or suspension of said compound is further treated with an activated carbon reagent such as, but not limited to, Darco KB-B. In one embodiment of this aspect, the transition metal impurity concentration reduced is palladium or an ion thereof. In another embodiment of this aspect, the transitional metal impurity concentration reduced is Zn or an ion thereof. In another embodiment of this aspect, the transition metal impurity concentration reduced is iron or an ion thereof. In a preferred embodiment, the transition metal impurity concentration in the compound of Formula (I) is reduced. In another preferred embodiment, the transition metal impurity concentration in the compound of Formula (III) is reduced. In another preferred embodiment, the transition metal impurity concentration in the compound of Formula (IV) is reduced. In a particularly preferred embodiment, the transition metal concentration impurity of the compound in Formula (III) is reduced wherein the transition metals are palladium, zinc, and/or iron; or an ion thereof. Typically, the mole ratio of metal chelating agent to the compound of Formula (I), Formula (III) or Formula (IV) is about 1:1 to about 1:20, more typically about 1:5 to about 1:10. In a preferred embodiment, the metal chelating agent is an alkali metal salt of ethylenediaminetetraacetic acid. Typically, the weight ratio of activated carbon reagent to the compound of Formula (I), Formula (III), or Formula (IV) is about 1:5 to about 1:1. Typically, the palladium impurity concentration in a compound of Formula (I), Formula (III), or Formula (IV) is reduced to below 500 ppm, more typically 100 ppm. Typically, the iron and/or zinc impurity concentration in a compound of Formula (I), Formula (III), or Formula (IV) is reduced to below 10,000 ppm, more typically below 1000 ppm.

The compound of Formula (VIII) can be prepared by the reaction of an appropriately 5-substituted 2,4,6-trichloropyrimidine (e.g., 2,4,6-trichloro-5-alkyl-pyrimidine) with an alkoxide or alkoxyaryl reagent (e.g., NaOMe, NaOEt, etc.).

5-Substituted 2,4,6-trichloropyrimidines can be prepared by chlorination of an appropriately 5-substituted barbituric acid (e.g., chlorination with $SOCl_2$ or $P(O)Cl_3$).

5-Substituted barbituric acid compounds can be prepared by the cyclization of 2-substituted malonate esters (e.g., diethyl isopropyl malonate) with urea in the presence of a base (e.g., an alkali metal alkoxide such as NaOEt).

2-Substituted malonate esters can be prepared by the reaction of a malonate ester with, e.g. an alkylating agent such as 2-bromopropane, in the presence of a base, e.g., an alkali metal alkoxide such as NaOEt.

3-Chloro-5-methylbenzyl cyanide, 3-bromo-5-methylbenzyl cyanide or 3-iodo-5-methylbenzyl cyanide can be prepared by any suitable method, for example by brominating 3,5-dimethyl chlorobenzene, 3,5-dimethyl bromobenzene or 3,5-dimethyl iodobenzene, e.g., with NBS/benzoyl peroxide, to form 1-chloro-3-(bromomethyl)-5-methylbenzene, 1-bromo-3-(bromomethyl)-5-methylbenzene or 1-iodo-3-(bromomethyl)-5-methylbenzene, respectively. The 1-chloro-3-(bromomethyl)-5-methylbenzene, 1-bromo-3-(bromomethyl)-5-methylbenzene or 1-iodo-3-(bromomethyl)-5-methylbenzene can then be converted to 3-chloro-5-methylbenzyl cyanide, 3-bromo-5-methylbenzyl cyanide or 3-iodo-5-methylbenzyl cyanide, respectively, by reaction with cyanide ion (e.g., KCN).

ADDITIONAL EMBODIMENTS

1. A method of preparing a compound of Formula (I):

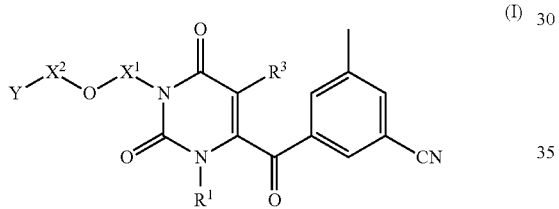

(I)

or a pharmaceutically acceptable salt thereof, wherein:
$R^1$ and $R^3$ are each independently H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, or substituted heterocyclyl, arylalkyl, substituted arylalkyl, heteroarylalkyl; or substituted heteroarylalkyl;
$X^1$ is alkylene, substituted alkylene, alkenylene, substituted alkenylene, alkynylene, substituted alkynylene, carbocyclylene, substituted carbocyclylene, heterocyclylene, or substituted heterocyclylene;
$X^2$ is a covalent bond, alkylene, or substituted alkylene;
Y is selected from a group consisting of:

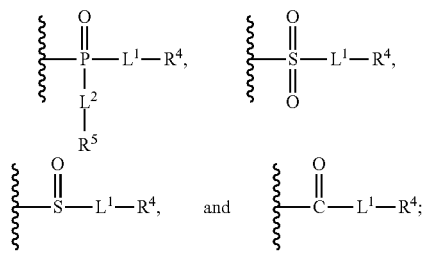

$L^1$ and $L^2$ are each independently a covalent bond, C—, or —$NR^6$—;

$R^4$ and $R^5$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—$R^7$, -(substituted alkylene)-C(O)—O—$R^7$, -alkylene-O—C(O)—O—$R^7$, or -(substituted alkylene)-O—C(O)—O—$R^7$; and $R^6$ and $R^7$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl; comprising:

(d) reacting a compound of Formula (II) wherein G is Cl, Br or I with a cyanide reagent:

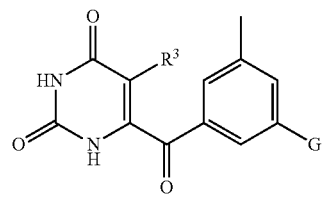

(II)

thereby forming a compound of Formula (III):

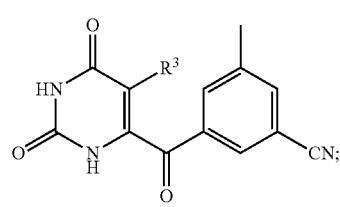

(III)

(e) reacting the compound of Formula (III) with $R^1Z^1$, wherein $Z^1$ is a leaving group, thereby forming a compound of Formula (IV):

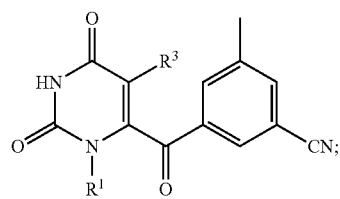

(IV)

(f) reacting the compound of Formula (IV) with Y—$X^2$—O—$X^1$—$Z^2$, wherein $Z^2$ is a leaving group, thereby forming the compound of Formula (I).

2. The method of embodiment 1, wherein the cyanide reagent of step (d) comprises a palladium(0) or palladium(II) catalyst and a cyanide ion source.

3. The method of embodiments 1 or 2 wherein the cyanide reagent comprises a cyanide ion source selected from the group consisting of alkali metal cyanides, alkaline earth cyanides, transition metal cyanides, CuCN, Zn(CN)$_2$, potassium hexacyanoferrate, trialkylsilylcyanide, acetone cyanohydrin, and benzylthiocyanate.

4. The method of any one of embodiments 1 to 3 wherein the cyanide reagent comprises the palladium(0) or palladium(II) catalyst selected from the group consisting of $Pd_2dba_3$, $Pd(dba)_2$, $PdBr_2$, $PdCl_2$, $Pd(acetate)_2$, $Pd(trifluoroacetate)_2$, $Pd(triphenylphosphine)_4$, $PdCl_2(triphenylphosphine)_2$, $Pd(tri\text{-}tert\text{-}butylphosphine)_2$ and Pd on carbon.

5. The method of any one of embodiments 1 to 4 wherein the cyanide reagent further comprises a phosphine-containing ligand selected from the group consisting of 1,1'-bis(diphenylphosphino)ferrocene (DPPF), di(1-admamantyl)-1-butylphosphine, 2-di-tert-butylphosphino-1,1'-binaphthyl, 2-(dicyclohexylphosphino)-2',6'-dimethoxy-1,1'-biphenyl (S-Phos), 2-(dicyclohexylphosphino)-2',4',6'-tri-iso-propyl-1,1'-biphenyl (X-Phos), 1,5-bis(diphenylphosphino)pentane, tri(cyclohexyl)phosphine, triphenylphosphine and tri(butyl)phosphine.

6. The method of any one of embodiments 1 to 5 wherein the cyanide reagent comprises a cyanide ion source that is $Zn(CN)_2$.

7. The method of any one of embodiments 1 to 6 wherein C of Formula (II) is Br.

8. The method of any one of embodiments 1 to 7, wherein each $R^1$ and $R^3$ is independently alkyl.

9. The method of any one of embodiments 1 to 8, wherein Y is:

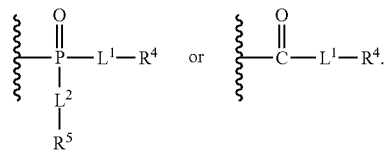

10. The method of any one of embodiments 1 to 9, wherein $Y-X^2-O-X^1-Z^2$ is alkyl-C(O)-O-alkylene-$Z^2$, and $Z^2$ is Br or I.

11. The method of any one of embodiments 1 to 10, wherein $Y-X^2-O-X^1-Z^2$ is $CH_3-C(O)-O-CH_2-Br$ or $CH_3-C(O)-O-CH_2-I$.

12. The method of any one of embodiments 1 to 11, wherein:
 $R^1$ is ethyl;
 $R^3$ is isopropyl; and
 $Y-X^2-O-X^1-Z^2$ is $CH_3-C(O)-O-CH_2Br$.

13. The method of any one of embodiments 1 to 12, wherein $R^1Z^1$ is an alkylating agent selected from the group consisting of alkyd bromides, alkyl iodides, alkyl alkylsulfonates, alkyl arylsulfonates, alkyl triflates, alkyl carbonates, alkyl fluorosulfonates, and dialkyl sulfates.

14. The method of any one of embodiments 1 to 13, further comprising:
 (c) preparing the compound of Formula (II) by hydrolyzing a compound of Formula (VI):

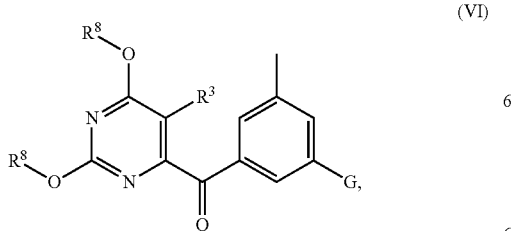

wherein each $R^8$ is a hydroxyl protecting group.

15. The method of embodiment 14, further comprising:
 (b) preparing the compound of Formula (VI) by the oxidation of a compound of Formula (VII):

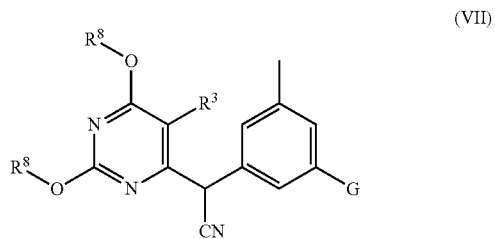

wherein each $R^8$ is a hydroxyl protecting group.

16. The method of embodiment 15, further comprising:
 (a) reacting a compound of Formula (VIII):

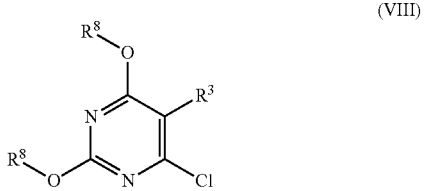

with 3-chloro-5-methylbenzyl cyanide, 3-bromo-5-methylbenzyl cyanide or 3-iodo-5-methylbenzyl cyanide.

17. The method of any one of embodiments 14 to 16, wherein each $R^8$ is independently alkyl or arylalkyl.

18. The method of any one of embodiments 1 to 17 wherein the cyanide reagent comprises $Pd_2dba_3$, DPPF and $Zn(CN)_2$.

19. The method of any one of embodiments 1 to 18 further comprising treating the compound of Formula (III) with a metal chelating agent and an activated carbon reagent.

20. The method of any one of embodiments 15 to 18, wherein the oxidation comprises a reaction with an alkali metal hydride and $O_2$.

EXAMPLES

Exemplary methods for preparing the compounds of Formula (I) are provided below. These methods are intended to illustrate the nature of such preparations and are not intended to limit the scope of applicable methods. While the examples specify certain reaction conditions, one skilled in the art will understand how to vary the specific reaction conditions to obtain the full scope of the invention.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example; boiling point and molecular weight for distillation and sublimation, presence or absence of polar functional groups for chromatography, stability of materials in acidic and basic media in multiphase extractions; and the like. One skilled in the art will apply techniques most likely to achieve the desired separation.

LIST OF ABBREVIATIONS AND ACRONYMS

| Abbreviation | Meaning |
| --- | --- |
| AIBN | 2,2'-azobis(2-methylpropionitrile) |
| % AN | area norm, i.e. % of total area under an integrated curve |
| Bn | benzyl |
| BnBr | benzylbromide |
| BSA | bis(trimethylsilyl)acetamide |
| BzCl | benzoyl chloride |
| CDI | carbonyl diimidazole |
| dba | dibenzylideneacetone |
| DCC | dicyclohexylcarbodiimide |
| DIPEA | di-isopropylethylamine |
| DMAP | 4-dimethylaminopyridine |
| DMA or DMAC | N,N-dimethylacetamide |
| DMTCl | dimethoxytrityl chloride |
| DMSO | dimethylsulfoxide |
| DMF | dimethylformamide |
| EtOAc | ethyl acetate |
| ESI | electrospray ionization |
| HMDS | hexamethyldisilazane |
| HPLC | High pressure liquid chromatography |
| LDA | Lithium diisopropylamide |
| LRMS | low resolution mass spectrum |
| mCPBA | meta-chloroperbenzoic acid |
| MeOH | methanol |
| m/z or m/e | mass to charge ratio |
| $MH^+$ | mass plus 1 |
| $MH^-$ | mass minus 1 |
| MsOH | methanesulfonic acid |
| MS or ms | mass spectrum |
| NBS | N-bromosuccinimide |
| NMP | N-methylpyrollidinone |
| rt or r.t. | room temperature |
| TMSCl | chlorotrimethylsilane |
| TMSBr | bromotrimethylsilane |
| TMSI | iodotrimethylsilane |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| δ | parts per million down field from tetramethylsilane |

Example 1

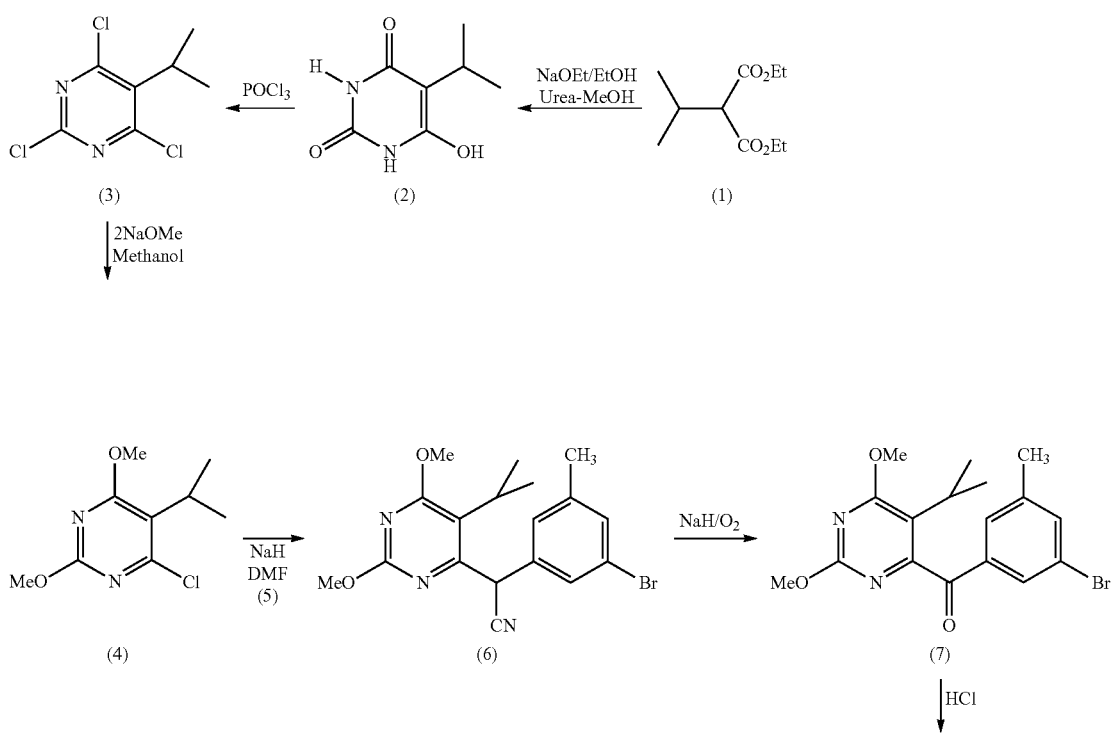

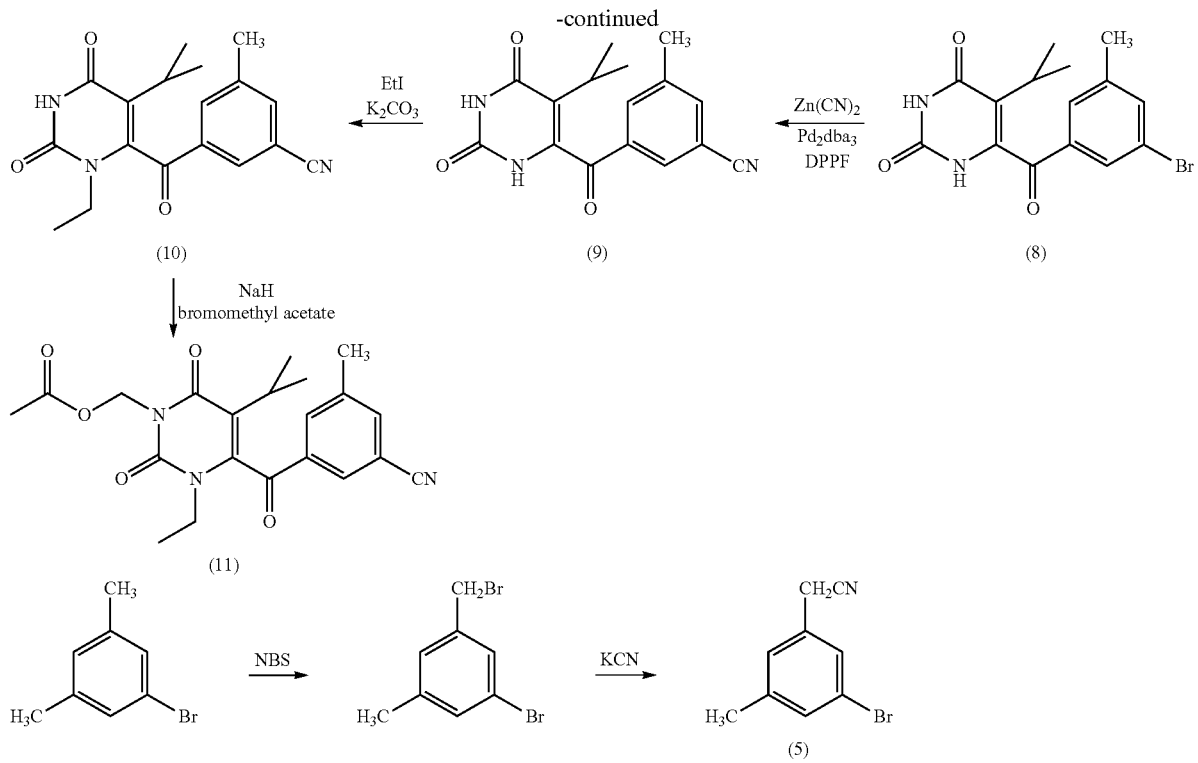

Step 1:

To a stirred solution of 21 wt. % sodium ethoxide (245 mL, ~0.6 M), was added diethyl malonate (80 mL, 0.5 M). Immediately, a white precipitate formed. The mixture was then heated to reflux (the white precipitate dissolved during this process) and 2-bromopropane (70 mL, 0.75 M) was added dropwise during 30-45 min. Refluxing was continued for over 10 hr. After cooling to room temperature, the mixture was evaporated in vacuo. The residue was dissolved in ether, washed with saturated $NH_4Cl$ solution, dried with $MgSO_4$, filtered, and evaporated in vacuo to give 98 g (97%) of diethyl isopropyl malonate (1) as a pale brown oil. The crude product was used directly in the next reaction.

$^1$H NMR (200 MHz, $CDCl_3$) δ 0.98 (6H, d, J=6.6 Hz), 1.25 (6H, t, J=7.2 Hz), 2.32-2.43 (1H, m), 3.09 (1H, d, J=8.6 Hz), 4.17 (4H, q, J=7.2 Hz).

Step 2:

Sodium pieces (11.5 g, 0.5 M) were reacted with ethanol (300 mL) under nitrogen. Diethyl isopropyl malonate (1) (97 g, 0.48 M, crude product) was added to the solution. Urea (30 g, 0.5 M) in hot methanol (100 mL+10 mL for washing) was then added. A yellow precipitate formed immediately. The mixture was heated to reflux and refluxing was continued overnight (~20 hr). The mixture was evaporated in vacuo and the residue was dissolved in water (100 mL) and cooled in an ice bath. Conc. HCl (43 mL, pH paper 3~4) was added to the solution and stirred for 2 hr. The precipitate was collected by filtration, washed with ice-cold water (200 mL) twice, cold ethanol (200 mL), ether (excess), and dried in vacuo to give 49 g (58%) of 5-isopropylbarbituric acid (2) as a white solid.

$^1$H NMR (200 MHz, DMSO-$d_6$) δ 0.98 (6H, d, J=7.0 Hz), 2.41 (4H, m), 3.19 (1H, d, J=3.6 Hz), 11.20 (2H, s).

Step 3:

5-isopropylbarbituric acid (2) (75 g, 0.44 M) was added to phosphorus oxychloride (150 mL), and the mixture was cooled in a water bath. N,N-diethylaniline (210 mL, 1.32 M) was then added dropwise (this process was observed to be exothermic, and the mixture solidified). After 1-2 hr., the reaction mixture was heated in an oil bath (~140-150° C.) for 7 hr (the solid melted at ~110-120° C.). After cooling to room temperature, the mixture was poured into an excess of crushed ice. A pale yellow precipitate formed immediately.

After standing at room temperature until the ice melted completely, the precipitate was filtered and washed with water (500 mL) three times. The solid was then dissolved in hexane, washed with water twice, washed with sat. aqueous sodium bicarbonate solution, dried with anhydrous magnesium sulfate, filtered, and evaporated in vacuo to afford crude 5-isopropyl-2,4,6-trichloropyrimidine (3) (92.4 g, 93%) as a pale yellow solid.

The crude (3) was dissolved in ether (100 mL) and diluted with methanol (100 mL). The mixture was then concentrated as much as possible. The precipitate was filtered, washed with cold methanol, and dried in vacuo to afford 65 g (65%) of (3) as a white solid. From the residue, an additional 16.7 g (16.8%) of (3) was obtained after repeating this procedure.

m.p. 70-71° C.; $^1$H NMR (200 MHz, $CDCl_3$) δ 1.44 (6H, d, J=7.2 Hz), 3.76 (1H, m); $^{13}$C NMR (50 MHz, $CDCl_3$) δ 18.69, 29.49, 135.19, 155.99, 162.20; m/z (EI) 225 ($M^+$)

Step 4:

To a stirred, anhydrous methanol (600 mL) at room temperature, was added sodium metal pieces (24.7 g, 1.074 M) during 1 hr. After completion of the reaction, the solution was cooled in an ice bath and 5-isopropyl-2,4,6-trichloropyrimidine (121.08 g, 0.537 M) was added portion-wise (over 20~25 min.). After 1 hr., the ice bath was removed and the mixture was stirred at room temperature overnight. The mixture was evaporated in vacuo and the residue was dissolved in ether, washed with water, dried with $MgSO_4$, filtered, and evaporated in vacuo. The residue was purified by silica gel column chromatography (eluent: 3:97 ether/hexane) to afford 105 g (90%) of 6-chloro-2,4-dimethoxy-5-isopropylpyrimidine (4) as a colorless oil.

m.p. 23-24° C.; $^1$H NMR (200 MHz, CDCl$_3$) δ1.23 (6H, d, J=7.1 Hz), 3.39 (1H, m), 3.94 (3H, s), 3.97 (3H, s); $^{13}$C NMR (50 MHz, CDCl$_3$) δ19.61, 27.30, 54.19, 54.83, 117.33, 158.59, 161.69, 170.05; m/z (EI) 216 (M$^+$)

Step 5:

A mixture of 3,5-dimethylbromobenzene (70 g, 0.378 M), NBS (67.3 g, 0.373 M), and benzoyl peroxide (2.27 g, 0.009 M) in carbon tetrachloride (300 mL) was refluxed for 3 hr. After cooling to room temperature, the mixture was filtered and the filtrate was evaporated in vacuo to give a pale brown oil. The crude product was dissolved in hexane and filtered through a short silica gel pad (diameter: 9.5 cm, height: 7 cm). The silica gel pad was washed with hexane until the product eluted completely. The filtrate was evaporated in vacuo to give 94 g of 1-bromo-3-(bromomethyl)-5-methylbenzene (contaminated with starting material and 1-bromo-3,5-bis-bromomethylbenzene) as a pale brown oil, which solidified on standing at room temperature. The mixture was used directly in the next reaction without further purification.

(NMR of purified product): $^1$H NMR (200 MHz, CDCl$_3$) δ 2.32 (3H, s), 4.39 (2H, s), 7.12 (1H, s), 7.26 (1H, s), 7.34 (1H, s).

Step 6:

The crude 1-bromo-3-(bromomethyl)-5-methylbenzene obtained from step 5 (188 g, ~0.71 M) was dissolved in ethanol (470 mL) by warming in an oil bath (50-60° C.). Potassium cyanide (69.57 g, 1.068 M) was added, then distilled water (235 mL). The mixture was heated to reflux and stirred for 3 hr. After cooling to room temperature, the mixture was evaporated in vacuo and the residue was diluted with ether, washed with water, dried with MgSO$_4$, filtered, and evaporated in vacuo. The residue was dissolved in dichloromethane and ethyl acetate-hexane (1:20) and loaded onto a silica gel column and eluted with ethyl acetate-hexane (from 1:20 to 1:6) to afford 85 g (53% for 2 steps) of 3-bromo-5-methylbenzyl cyanide (5) as a pale brown oil.

$^1$H NMR (200 MHz, CDCl$_3$) δ 2.34 (3H, s), 3.68 (2H, s), 7.08 (1H, s), 7.27 (1H, s), 7.29 (1H, s).

Step 7:

To a stirred mixture of 6-chloro-2,4-dimethoxy-5-isopropylpyrimidine (4) (47.63 g, 0.22 M) and 3-bromo-5-methylbenzyl cyanide (5) (42 g, 0.2 M) in anhydrous DMF (220 mL) in an ice bath under an atmosphere of nitrogen, was added portion-wise 60% sodium hydride (16 g, 0.4 M) over 2 hr. (Vigorous foaming occurred during the addition of the second half of the NaH). After stirring for 1 hr., the mixture was stirred at room temperature overnight. The mixture was neutralized with saturated ammonium chloride solution. The crude product was extracted with ether and purified by silica gel column chromatography (eluent, ether:hexane (from 1:9 to 1:7)) to afford 63.66 g (81.6%) of (6) as a white solid. (The yield is an average of 6 reactions.)

m.p. 123-124° C.; $^1$H NMR (200 MHz, CDCl$_3$) δ 1.11 (3H, d, J=6.9 Hz), 1.15 (34, D, J=6.9 Hz), 2.32 (3H, s), 2.97 (1H, m), 4.00 (3H, s), 4.01 (3H, s), 5.34 (1H, s), 7.14 (1H, s), 7.28 (1H, s), 7.31 (1H, s).

Alternative Step 7:

To a stirred mixture of 6-chloro-2,4-dimethoxy-5-isopropylpyrimidine (4) (86.44 g, 0.399 M) and 3-bromo-5-methylbenzyl cyanide (5) (80 g, 0.38 M) in anhydrous DMF (380 mL) in an ice bath under an atmosphere of nitrogen, was added portion-wise 95% potassium t-butoxide (96 g, 0.812 M) over 1 hr. After stirring for 1 hr., the ice bath was removed and the mixture was stirred at room temperature for overnight (~16 hr.). The mixture was cooled in a water bath and neutralized with saturated ammonium chloride solution (200 mL). The mixture was diluted with water (200 mL). The orange precipitate was collected by filtration and washed with water (1.5 L). The crude product obtained from two reactions was combined and worked up as follows:

The crude product was dissolved in dichloromethane (500 mL), washed with water, dried with MgSO$_4$, filtered, and concentrated to give a brown syrup. The syrup, with stirring, was then diluted with ethyl acetate-hexane (1:14, 1 L) and stirred with some seed crystals in an ice bath for 3 hr. The precipitate was collected by filtration, washed with hexane, and dried in vacuo to give 181 g (61%) of (6) as a pale yellow solid.

Step 8:

To a stirred solution of (6) (200 g, 0.512 M) in anhydrous DMF (400 mL) in a water bath under nitrogen, was added portion-wise 60% sodium hydride (21.52 g, 0.538 M) over 30 min. After stirring for 40 min. under nitrogen, oxygen gas was bubbled into the reaction mixture for 2.5 hr (TLC: ethyl acetate/hexane (1:9) or ether/hexane (1:9)) showed no starting material; mildly exothermic reaction). The mixture was neutralized with saturated ammonium chloride solution (400 mL) and diluted with water (800 mL). The precipitate was collected by filtration, washed with water (2 L) to give a pale yellow solid (wet amount: 240 g, theoretical yield=194 g). The crude (7) was used directly in the next reaction step without further purification.

(Further Purified Product): m.p. 122-123° C.; $^1$H NMR (200 MHz, CDCl$_3$) δ 1.17 (6H, d, J=7.1 Hz), 2.36 (3H, s), 2.77 (1H, m), 3.92 (3H, s), 4.05 (3H, s), 7.54-7.56 (2H, m), 7.75 (1H, m).

Step 9:

The wet crude (7) (~97 g, 0.2557 M) was refluxed with dioxane/conc. HCl (1:1, 400 mL) for 3 hr. After cooling to room temperature, the mixture was diluted with water (500 mL) and the white precipitate was collected by filtration, and washed with water. The solid was suspended in ethanol (300 mL), filtered, washed with ethanol (200 mL) and hexane (300 mL), and dried under high vacuum to give 84 g (93% for two steps) of (8) as a white solid.

m.p. 266-267° C.; $^1$H NMR (200 MHz, DMSO-d$_6$) δ 1.05 (6H, d, J=6.8 Hz), 2.26 (1H, m), 2.40 (3H, s), 7.82 (2H, s), 7.93 (1H, s), 11.02 (1H, s), 11.17 (1H, s).

Step 10:

To a stirred solution of (8) (70.2 g, 0.2 M) in anhydrous DMF (200 mL) under nitrogen, were added zinc cyanide (14.08 g, 0.12 M), DPPF (1,1'-bis(diphenylphosphino)ferrocene) (2.4 g, 4.33 mmol), and Pd$_2$dba$_3$ (1.82 g, 1.987 mmol) in this order. The mixture was then heated to 110-120° C. (oil bath temperature) over 1 hr., and the mixture was stirred for 7 hr. at that temperature. TLC (ethyl acetate:hexane (1:1)) showed no starting material after 5 hr. After cooling to room temperature, the mixture was cooled in an ice bath. The mixture, with vigorous stirring, was gradually diluted with 4:1:4 v/v/v saturated aq. NH$_4$Cl—NH$_4$OH-water (600 mL) during 20 min. After stirring for 2 hr., crude product was collected by filtration, washed with 4:1:4 v/v/v saturated aq. NH$_4$C$_1$—NH$_4$OH-water (600 mL) and water (600 mL). The crude product was suspended in ethanol (300 mL) and evaporated in vacuo. The residue was co-evaporated with toluene (200 mL). The residue was then suspended in toluene (200 mL and warmed up for ~1 hr. After cooling to room temperature, the mixture was stirred in an ice bath for 30 min. The precipitate was collected by filtration, washed with toluene (200 mL) and hexane (200 mL), and dried in vacuo to afford 48.6 g (82%) of (9) as a grey solid. This compound was used to the next reaction step without further purification.

$^1$H NMR (200 MHz, DMSO-d$_6$) δ1.02 (6H, d, J=6.6 Hz), 2.24 (1H, m), 2.44 (3H, s), 8.04 (1H, s), 8.10 (1H, s), 8.33 (1H, s); m/z (EI) 297 (M$^+$)

Alternative Conditions for Step 10:

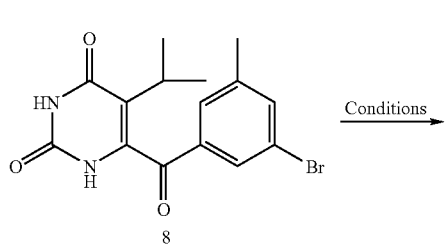

Conditions

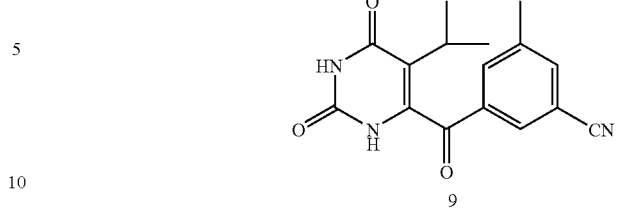

TABLE 1

Addition of Zn additives and alternative ligands for cyanation of 8.

| Experiment | Degas | Zinc | Zinc Acetate | Ligand | Solvent | % AN 9 | |
|---|---|---|---|---|---|---|---|
| 1 | — | — | — | DPPF | Anhydrous DMF | 75 | (2 h, 120° C.) |
|   |   |   |   |   |   | 95 | (4 h, 120° C.) |
| 2 | — | — | — | DPPF | DMF (0.05% $H_2O$) | 4 | (16 h, 100-120° C.) |
| 3 | Yes | — | — | DPPF | DMF (0.05% $H_2O$) | 81 | (2 h, 100° C.) |
|   |   |   |   |   |   | 96 | (4 h, 100° C.) |
| 4 | — | Yes | — | DPPF | DMF | 64 | (2 h, 100° C.) |
|   |   |   |   |   |   | 94 | (4 h, 100° C.) |
| 5 | — | Yes | Yes | DPPF | DMF | 94 | (1 h, 100° C.) |
| 6 | — | Yes | — | — | DMF | 0.6 | (o/n, 100° C.) |
| 7 | — | Yes | — | $P(Bu)_3$ | DMF | 4 | (o/n, rt) |
| 8 | — | Yes | — | $P(Ph)_3$ | DMF | 94 | (o/n, rt-100° C.) |

$Pd_2dba_3$ and $Zn(CN)_2$ used in all reactions.

TABLE 2

Variation of reaction solvent and temperature for generating 9.

| Experiment | Degas | Zinc | Zinc Acetate | Temp (° C.) | Solvent | % AN 9 |
|---|---|---|---|---|---|---|
| 9 | Yes | — | — | 100 | DMF | 81 (2 h), 96 (4 h) |
| 10 | Yes | — | — | 100 | DMAC | 95 (2 h) |
| 11 | Yes | — | — | 100 | NMP | 66 (2 h), 96 (17 h) |
| 12 | Yes | — | — | 80 | DMF | 15 (2 h), 21 (21 h) |
| 13 | — | Yes | Yes | 80 | DMF | 94 (2 h) |
| 14 | — | Yes | Yes | 80 | DMAC | 94 (2 h) |
| 15 | — | Yes | Yes | 80 | NMP | 80 (2 h) |
| 16 | — | Yes | Yes | 60-70 | DMF | 13 (1 h, 60° C.), 90 (20 h, 70° C.) |
| 17 | Yes* | — | — | 120 | DMF | 94 (1 h) |
| 18 | Yes* | — | — | 120 | DMAC | 96 (1 h) |

*Degassing done by repeated vessel evacuation and subsequent $N_2$ purge. $Pd_2dba_3$ DPPF and $Zn(CN)_2$ were used in all reactions.

TABLE 3

Cyanation reaction outcome of 8 with and without 1% water.

| Experiment | 8 (g) | 1% $H_2O$ Added | % AN 9 | % AN 8 | Comments |
|---|---|---|---|---|---|
| 19 | 0.72 | — | 28 (2 h) | 69 (2 h) | Reaction Stalled |
| 20 | 42.5 | — | 62 (1 h), 93 (3.5 h) | 34 (1 h), 3 (3.5 h) | Reaction Stalled |
| 21 | 100 | Yes | 96 (0.5 h) | <1 | — |
| 22 | 300 | Yes | (complete) TLC | (absent) TLC | Complete Conversion |

TABLE 3-continued

Cyanation reaction outcome of 8 with and without 1% water.

| Experiment | 8 (g) | 1% H$_2$O Added | % AN 9 | % AN 8 | Comments |
|---|---|---|---|---|---|
| 23 | 33 | Yes | 95 (2 h) | <1 | 86% isolated yield |

Pd$_2$dba$_3$ (0.01 eq), DPPF (0.02 eq), Zn(CN)$_2$ (0.6 eq), and DMF (1M) were used in all reactions.

Step 11:

Compound (9) (48.6 g, 0.1636 M) was stirred with powdered anhydrous potassium carbonate (27.12 g, 0.196 M) in DMF (325 mL) at room temperature under nitrogen. After 50 min., iodoethane (17 mL, 0.2105 M) was added rapidly by syringe and the stirring was continued for ~18 hr. The mixture was evaporated in vacuo and the residue was treated with 10% methanol-dichloromethane and filtered through a celite pad and the filtrate was evaporated in vacuo. The residue (dissolved in dichloromethane and loaded onto a silica gel column) was purified by silica gel column chromatography (eluent: ethyl acetate/hexane (1:2), TLC (ethyl acetate/hexane (2:3)) to afford 34 g (64%) of (10) as a white solid. The product was further purified by recrystallization from chloroform-ether (1:3~1:4) (>95% recovery).

$^1$H-NMR (200 MHz, CDCl$_3$) δ 1.11-1.23 (9H, m), 2.23 (1H, m), 2.53 (3H, s), 3.18 (1H, m), 3.89 (1H, m), 7.80 (1H, s), 7.96 (1H, s), 8.06 (1H, s), 9.22 (1H, s); m/z (EI) 325 (M$^+$).

Alternative Process for Step 11:

A 3-neck flask was charged with 9 (6.15 g, 20.7 mmol), MeCN (36 mL) and stirred for 30 minutes. DIPEA (14.41 mL, 82.7 mol) was added to this mixture and it was heated to an internal temperature of 50° C. EtI was charged to flask and left stirring for 14 h. Reaction is monitored by HPLC and upon maximum conversion was cooled to RT and added acid-washed celite (12.3 g, 2S) and slurried for 1 hour. Slurry was filtered and washed with MeCN then acetone. The filtrate is concentrated to 2 S MeCN (12 mL) and was added H$_2$O (60 mL) and this slurry was agitated for 16 hours then filtered and washed with H$_2$O (6 mL×3). This solid was charged into flask along with isopropanol (18 mL) and this slurry was heated to and kept at reflux for 4 hours. The reaction was cooled over 20 hours to RT. This slurry was filtered and washed with isopropanol (6 mL×3) and dried in an oven for 24 hours. 4.7 g (69.8%) of 10 was isolated.

Additional Reagent Combinations for Step 11 to room temperature, anhydrous powdered K$_2$CO$_3$ (41.4 g, 0.3 M) was added to the mixture and stirred for 1 hr. at ambient temperature. Ethyl iodide (24.2 mL, 0.3 M) was then added to the mixture and the mixture was stirred in an oil bath (50-60° C.) for 24 hr. K$_2$CO$_3$ (12.42 g, 0.09 M) and ethyl iodide (7.2 mL, 0.9 M) were added again and the stirring was continued in an oil bath (50-60° C.) for 5 hr. After cooling to room temperature, the mixture was diluted with dichloromethane (400 mL) and filtered through a celite pad and the pad was washed with dichloromethane (~400 mL). The filtrate was washed with water (~800 mL) 4 times, dried with MgSO$_4$, filtered, and evaporated in vacuo to give a brownish-black syrup (~69 g). The residue was dissolved in dichloromethane and loaded into a silica gel column and eluted with ethyl acetate-hexane (1:2) to afford 38.67 g (59% for 2 steps) of (10) as a pale brown solid.

$^1$H NMR (200 MHz) and Mass (EI) 325 (M+), 326 (M+1$^+$), 327 (M+2$^+$) was identical with (10) prepared as described in steps 8-11, above.

Preparation of Compound (11)

To a stirred solution of (10) (41.238 g, 0.1267 M) in DMF (190 mL) in an ice bath, was added 60% NaH (6.08 g, 0.152 M) portion-wise over 30 min. After 20 min., the mixture was stirred at room temperature for 30 min. The mixture was then cooled in an ice bath and acetic acid bromomethyl ester (15.7 mL, 0.152 M) was added within 5 min. Within 40 min., the mixture solidified (TLC showed just a small amount of starting material). The reaction mixture was stirred at room temperature overnight, concentrated, and the residue dissolved in dichloromethane and filtered through a celite pad. The celite pad was washed with dichloromethane several times. The filtrate was concentrated in vacuo. The residue was dissolved in a minimum volume of dichloromethane and loaded onto a silica gel column and eluted with ethyl acetate-hexane (1:2). After running the column 4 times, 45 g (90%) of (11) was obtained as a white solid.

| Solvents | Bases | Equiv. | Alkylating Agents | Equiv. | Temp (° C.) |
|---|---|---|---|---|---|
| DMF | K$_2$CO$_3$ | 1-10 | Ethyl Iodide | 0.5-3 | RT-reflux |
| THF | Pyridine | | Ethyl Bromide | | |
| MeCN | Triethylamine | | Diethyl Sulfate | | |
| Acetone | dipea | | Ethyl Tosylate | | |
| (~10 vol.) | NaHMDS | | Diethylcarbonate | | |
| | KOtBu | | | | |

Alternative One-Pot Process for Preparing (10) Combing Steps 8-11:

To a stirred solution of (6) (70.2 g, 0.2 M) in anhydrous DMF (200 mL) under nitrogen, were added zinc cyanide (14.08 g, 0.12 M), DPPF (2.4 g, 4.33 mmol), and Pd$_2$dba$_3$ (1.82 g, 1.987 mmol) in this order. The mixture was then heated to 110-120° C. (oil bath temperature) over 1 hr. and the mixture was stirred for 6 hr. at that temperature. After cooling m.p. 180-181° C.; $^1$H NMR (200 MHz, CDCl$_3$): 8.05 (s, 1H), 8.00 (s, 1H), 7.81 (s, 1H), 6.04 (s, 2H), 3.83-4.01 (m, 1H), 3.10-3.28 (m, 1H), 2.54 (s, 3H), 2.24 (m, 1H), 2.14 (s, 3H), 1.11-1.23 (m, 9H). m/z (EI) 397 (M$^+$), 398 (M+1$^+$)

Alternative Preparation of Compound (11):

To a stirred solution of (10) (16.268 g, 0.05 M) in DMF (100 mL) in a water bath, was added 60% NaH (2.4 g, 0.06 M) portion-wise over 5 min. After 15 min., the mixture was stirred at room temperature for 20 min. The mixture was then cooled in an ice bath and acetic acid bromomethyl ester (6 mL, 0.0612 M) was added within 2 min. After 1 h, TLC showed only small amount of starting material. The mixture was stirred for a further 1 hr. in an ice-water bath. During this time, the mixture solidified. Water (200 mL) was then added to the mixture in an ice-water bath and stirring was continued for 2 hr. The green-colored precipitate was collected by filtration, and washed with water. The crude product was dissolved in dichloromethane (100 mL), washed with water, dried with MgSO$_4$, filtered, concentrated, and loaded onto a silica gel column, and eluted with ethyl acetate-hexane (1:2) to give 15.87 g (79.8%) of (11) as a white solid.

Recrystallization:

Compound (10) (48 g) was suspended in isopropanol (900 mL) and dissolved by heating to reflux on a hot plate. The solution was filtered through a glass funnel to remove a small amount of insoluble material. The solution was concentrated by heating on a hot plate until the total volume was reduced to a 750 mL volume. Distilled water was then added in 250 mL portions during 30 min (total volume of water added was 1500 mL). When 750 mL of water was added, the solution became turbid. After heating on a hot plate for 10 min., the solution was stirred for ~19 hr. at room temperature. The crystals were collected by filtration, washed with distilled water twice, and dried in vacuo for 18 hr. to afford 46 g (95.8%) of (11) as a white crystal.

m.p. 181-182° C.; $^1$H NMR (300 MHz, CDCl$_3$): 8.06 (s, 1H), 8.00 (s, 1H), 7.82 (s, 1H), 6.03 (s, 2H), 3.96-3.88 (m, 1H), 3.23-3.16 (m, 1H), 2.54 (s, 3H), 2.29-2.20 (m, 1H), 2.14 (s, 3H), 1.22 (d, J=6.8 Hz, 3H), 1.18-1.12 (m, 6H).

Example 2

Large-Scale Preparation of Compound (10) and Compound (II)

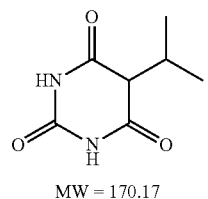

MW = 170.17

5-Isopropylbarbituric Acid

Sodium metal (1.28 kg, 55.65 mol) was dissolved in ethanol (25 L) under nitrogen atmosphere at 0° C. (bath temperature). Diethyl malonate (7.45 kg, 46.51 mol) was added to the solution and the mixture was heated to 80° C. 2-Bromopropane (8.00 kg, 65 mol) was added dropwise to the solution for 1 hour, and the solution was refluxed for 10 hours. The solution was cooled to room temperature. Sodium metal (1.22 kg, 53.04 mol) was dissolved into the solution under nitrogen atmosphere at 0° C. Urea (2.78 kg, 46.28 mol) in methanol (15 L) was added to the solution over 2 hours and the reaction mixture was refluxed for 20 hours. The reaction mixture was diluted with water (35 L) and conc. HCl (5 L), and cooled to room temperature. The precipitate was collected by filtration, washed with water (20 L), ether (15 L), n-hexane (20 L) and dried in vacuum at 40° C. for 10 hours to give 5-isopropyl-barbituric acid as a white solid (3.42 kg, 20.10 mol, 43% yield).

$^1$H NMR (300 MHz, DMSO-d$_6$) δ 1.08 (6H, d), 2.51 (1H, m) 3.28 (1H, m), 11.31 (2H, s).

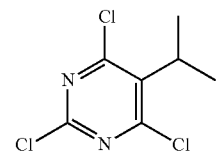

MW = 225.5

5-Isopropyl-2,4,6-trichloropyrimidine

5-Isopropyl barbituric acid (3.42 kg, 20.10 mol) was added to phosphorus oxychloride (8.0 L) at room temperature. To the mixture, N,N-diethylaniline (9.50 L) was added dropwise over 2 hours. After the addition was completed, the reaction mixture was heated to ~120-130° C. and stirred vigorously for 18 hours (the solid melted at around 110-120° C.). The reaction mixture was cooled to room temperature and then was poured into crushed ice water (40 L) with vigorous stirring. The resulting pale yellow precipitate was collected by filtration and dissolved in n-hexane (20 L). The hexane solution was washed with water (10 L), a saturated sodium bicarbonate solution (10 L), dried with magnesium sulfate (1 kg) and concentrated under reduced pressure to give a pale yellow solid. (4.24 kg, 18.80 mol, 94%)

$^1$H NMR (300 MHz, CDCl$_3$) δ 1.44 (6H, d, J=7.2 Hz), 3.76 (1H, m); m/z (EI) 225 (M+)

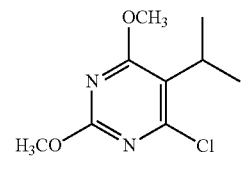

MW = 216.66

6-Chloro-2,4-dimethoxy-5-isopropylpyrimidine

To a stirred solution of 2,4,6-trichloropyrimidine (4.24 kg, 18.80 mol) in methanol (40 L), sodium methoxide was added portion-wise (2.11 kg 39.06 mol) at ~0-10° C. The reaction mixture was stirred at room temperature for 18 hours. The mixture was evaporated in vacuo and the residue was dissolved in n-hexane (20 L). The hexane solution was washed with water (10 L), dried with MgSO$_4$ (1 kg) and concentrated under reduced pressure. The residue was purified by silica gel column chromatography (eluent: ethyl acetate/hexane, 1:15) to give a pale brown oil. (2.72 kg, 12.55 mol, 66% yield)

$^1$H NMR (300 MHz, CDCl$_3$) δ 1.23 (6H, d, J=7.1 Hz), 3.39 (1H, m), 3.94 (3H, s), 3.97 (3H, s); m/z (EI) 216 (M+)

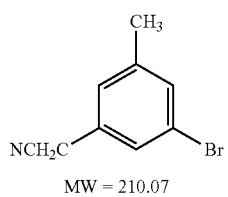

MW = 210.07

3-Bromo-5-methylbenzyl Cyanide

To a stirred solution of 3,5-dimethylbromobenzene (4.60 kg, 24.86 mol) in carbon tetrachloride (30 L) were added NBS (4.43 kg) and benzoyl peroxide (75 g) at room temperature. The reaction mixture was refluxed for 4 hours. After cooling to room temperature, the mixture was filtered and the filtrate was evaporated in vacuo to give a pale brown oil (6.56 kg). The resulting 1-bromo-3-(bromomethyl)-5-methylbenzene was not isolated but used directly in the next reaction step.

To a stirred solution of 1-bromo-3-(bromomethyl)-5-methylbenzene (6.56 kg, 0.1515 M) in ethanol (20 L) were added potassium cyanide (2.38 kg, 36.55 mol) and distilled water (10 L) in this order. The mixture was refluxed for 3 hours. After cooling to room temperature, the mixture was evaporated in vacuo and the residue was partitioned between ethyl acetate (30 L) and brine (20 L). The organic layer was dried with magnesium sulfate (2 kg) and concentrated under reduced pressure to give a brown-colored oil. The crude product was purified by silica gel column chromatography (eluent: ethyl acetate/hexane, 1:9) to afford 3-bromo-5-methylbenzyl cyanide (2.06 kg, 9.81 mol, 39%) as a pale brown oil.

$^1$H NMR (300 MHz, CDCl$_3$) δ 2.33 (3H, s), 3.68 (2H, s), 7.08 (1H, s), 7.28 (1H, s), 7.29 (1H, s).

(8)

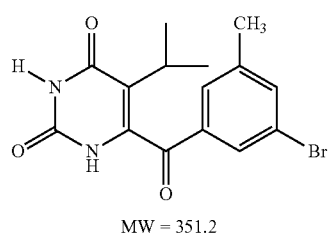

MW = 351.2

6-(3-Bromo-5-methylbenzoyl)-5-isopropylpyrimidine-2,4(1H,3H)-dione (8)

To a stirred solution of 6-chloro-2,4-dimethoxy-5-isopropylpyrimidine (2.54 kg, 11.72 mol) and 3-bromo-5-methylbenzyl cyanide (2.05 kg, 9.96 mol) in anhydrous DMF (20 L) was added 60% NaH (780 g) portion-wise over 4 hours under nitrogen atmosphere at 0° C. The reaction mixture was stirred at room temperature for 3 hours. After consumption of the starting materials (by TLC), the mixture was cooled down to 0° C.

To the above mixture was added 60% NaH (195 g) at 0° C. The reaction mixture was vigorously stirred for 18 hours at room temperature while oxygen gas was bubbled into the reaction mixture. After the disappearance of the starting material (by TLC), 48% HBr (8 L) was added to the reaction mixture. The reaction mixture was refluxed for 18 hours. After cooling to room temperature, the mixture was diluted with water (40 L). The resulting precipitate was collected by filtration, washed with water (15 L) and then was suspended in ethanol (15 L), filtered, washed with ethanol (5 L) and n-hexane (5 L). The solid was dried in vacuo to afford 6-(3-bromo-5-methylbenzoyl)-5-isopropylpyrimidine-2,4(1H,3H)-dione (2.14 kg, 6.09 mol, 62%) as a white solid.

1H-NMR (300 MHz, DMSO-d$_6$) δ 1.05 (6H, d, j=6.8 Hz), 2.26 (1H, m), 2.40 (3H, s), 7.82 (2H, s), 7.93 (1H, s), 11.02 (1H, s), 11.17 (1H, s); m/z (EI) 351 (M+)

(10)

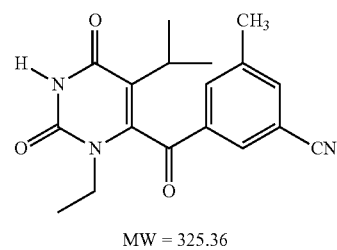

MW = 325.36

3-(3-Ethyl-5-isopropyl-2,6-dioxo-1,2,3,6-tetrahydropyrimidine-4-carbonyl)-5-methylbenzonitrile (10)

To a stirred solution of 6-(3-bromo-5-methylbenzoyl)-5-isopropylpyrimidine-2,4(1H,3H)-dione (2.14 kg, 6.09 mol) in anhydrous DMF (5 L) under nitrogen, were added zinc cyanide (428 g), DPPF (73 g), and Pd$_2$dba$_3$ (56 g), in this order. The mixture was heated to 110-120° C. and stirred vigorously for 2 hours. After cooling to room temperature, K$_2$CO$_3$ (1.88 kg) and iodoethane (1.15 L, 14.31 mol) were added to the mixture. The mixture was heated to 60-65° C. and stirred for 18 hours. After cooling to room temperature, the mixture was diluted with water (20 L). The precipitate was collected by filtration, washed with water (10 L) and then dissolved in dichloromethane (30 L). The solution was washed with water (10 L), 2N-HCl (10 L), dried with anhydrous magnesium sulfate (1 kg), and concentrated under reduced pressure. The crude product was purified by silica gel column chromatography (eluent: ethyl acetate/dichloromethane, 1:9) to afford 3-(3-ethyl-5-isopropyl-2,6-dioxo-1,2,3,6-tetrahydropyrimidine-4-carbonyl)-5-methylbenzonitrile (951 g, 2.92 mol, 48%) as a white solid.

$^1$H-NMR (300 MHz, CDCl$_3$) δ 1.11-1.23 (9H, m), 2.23 (1H, m), 2.53 (3H, s), 3.18 (1H, m), 3.89 (1H, m), 7.80 (1H, s), 7.96 (1H, s), 8.06 (1H, s), 9.22 (1H, s); m/z (EI) 325 (M+)

(11)

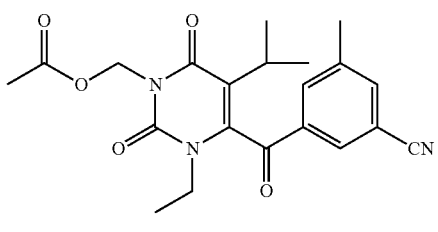

MW = 397.42

(4-(3-Cyano-5-methylbenzoyl)-3-ethyl-5-isopropyl-2,6-dioxo-2,3-dihydropyrimidin-1(6H)-ylmethyl acetate (11)

To a solution of 3-(3-ethyl-5-isopropyl-2,6-dioxo-1,2,3,6-tetrahydropyrimidine-4-carbonyl)-5-methylbenzonitrile (778 g, 2.39 mol) in anhydrous DMF (5 L) was added 60% NaH (115 g) portion-wise over 30 min at 0° C. The reaction mixture was stirred at room temperature for 3 hours and then the mixture was cooled to −10° C. Acetic acid bromomethyl ester (321 mL) was dropwise added to the reaction mixture for 2 hours at the same temperature and the reaction mixture was stirred at room temperature for 12 hours. The mixture was diluted with water (10 L). The precipitate was collected by filtration, washed with water (5 L) and then dissolved in dichloromethane (10 L). The organic solution was washed with water (4 L), dried with anhydrous magnesium sulfate (1 kg) and concentrated under reduced pressure. The crude product was purified by silica gel column chromatography (eluent: ethyl acetate/dichloromethane, 1:20) to give (4-(3-cyano-5-methylbenzoyl)-3-ethyl-5-isopropyl-2,6-dioxo-2,3-dihydropyrimidin-1(6H)-yl)methyl acetate (745 g, 1.87 mol, 79%) as a white solid.

Recrystallization:

4-(3-Cyano-5-methylbenzoyl)-3-ethyl-5-isopropyl-2,6-dioxo-2,3-dihydropyrimidin-1(6H)-yl)methyl acetate (745 g, 187 mol) was dissolved in refluxing isopropanol (12 L) and the insoluble material was removed by hot filtration. To the filtrate, distilled water (22 L) was added portion-wise for 1 hour to give a slightly cloudy solution, which was cooled from reflux to 25° C. over 2 hours. The resulting mixture was stirred at room temperature for 3 hours and the resulting crystalline material was collected by filtration, washed with distilled water (10 L) and dried in vacuo at 40° C. for 12 hours to give a white crystalline material (627 g, 1.58 mol, 84%).

1H NMR (300 MHz, CDCl$_3$): 8.05 (s, 1H), 8.00 (s, 1H), 7.81 (s, 1H), 6.04 (s, 2H), 3.83-4.01 (m, 1H), 3.10-3.28 (m, 1H), 2.54 (s, 3H), 2.24 (m, 1H), 2.14 (s, 3H), 1.11-1.23 (m, 9H); m/z (EI) 397 (M+), 398 (M+1).

Reduction of Transition Metal Ion Concentration in Compound 9

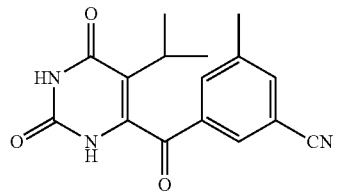

N,N-dimethylformamide (DMF) (94 ml) was purged with nitrogen for 1 h and then charged to a flask containing compound 8 (33.1 g, 94.2 mmol). Water (0.940 mL) was added followed by zinc cyanide (Zn(CN)$_2$) (6.636 g, 56.52 mmol) and then DMF (3 mL) to wash residual solids down the flask wall. To the mixture was added 1,1'-bis(diphenylphosphino)ferrocene (DPPF) (1.04 g, 1.87 mmol) followed by tris(dibenzylideneacetone)dipalladium (0) (Pd$_2$dba$_3$) (0.862 g, 0.941 mmol). The cloudy mixture was heated for 2 h at 117° C. After cooling to ambient temperature, ethyl acetate (240 mL) was added to the crude reaction mixture followed by 5% ethylenediaminetetraacetic acid disodium salt dihydrate (aq.) (95 mL). After brief agitation the mixture was passed through a pad celite to remove any gross solids followed by a wash with ethyl acetate (400 mL). The organics were separated and then washed twice with 18% brine (95 mL) followed by a wash with 5% ethylenediaminetetraacetic acid disodium salt dihydrate (aq.) (95 mL). The combined aqueous layer was back extracted with ethyl acetate (95 mL). To all combined organics was added Darco KB-B (28 g) and after 10 min the mixture was filtered through a pad of celite. The solvent was swapped for isopropanol and stripped to dryness. To the solid was added isopropanol (65 mL) followed by water (65 mL). The slurry was then filtered and the filter cake washed with isopropanol (35 mL). The solid was collected and dried overnight giving 24.1 g (86%).

All patents, patent applications, and other documents cited herein are hereby incorporated by reference in their entirety for all purposes.

We claim:
1. A method of preparing a compound of Formula (I):

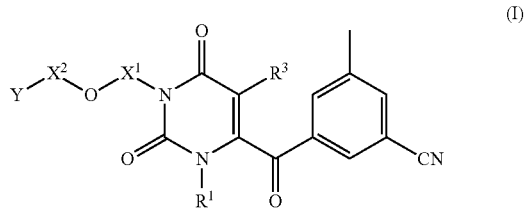

or a pharmaceutically acceptable salt thereof, wherein:
$R^1$ and $R^3$ are each independently H, alkyl, substituted alkyl, alkenyl, substituted alkenyl, alkynyl, substituted alkynyl, carbocyclyl, substituted carbocyclyl, aryl, substituted aryl, heteroaryl, substituted heteroaryl, heterocyclyl, or substituted heterocyclyl, arylalkyl, substituted arylalkyl, heteroarylalkyl; or substituted heteroarylalkyl;
$X^1$ is alkylene, substituted alkylene, alkenylene, substituted alkenylene, alkynylene, substituted alkynylene, carbocyclylene, substituted carbocyclylene, heterocyclylene, or substituted heterocyclylene;
$X^2$ is a covalent bond, alkylene, or substituted alkylene;
Y is selected from a group consisting of:

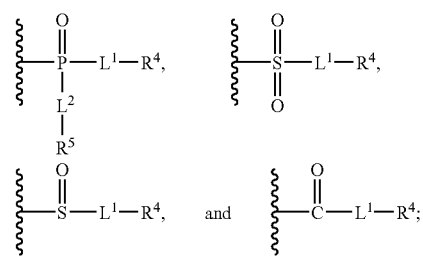

$L^1$ and $L^2$ are each independently a covalent bond, —O—, or —NR$^6$—;
$R^4$ and $R^5$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, substituted heterocyclylalkyl, -alkylene-C(O)—O—R$^7$, -(substituted alkylene)-C(O)—O—R$^7$, -alkylene-O—C(O)—O—R$^7$, or -(substituted alkylene)-O—C(O)—O—R$^7$; and
$R^6$ and $R^7$ are each independently H, alkyl, substituted alkyl, carbocyclyl, substituted carbocyclyl, heterocyclyl, substituted heterocyclyl, alkenyl, substituted alkenyl, alkynyl, substituted alkynyl, arylalkyl, substituted arylalkyl, heterocyclylalkyl, or substituted heterocyclylalkyl;

comprising:
(d) reacting a compound of Formula (II) wherein G is Cl, Br or I with a cyanide reagent:

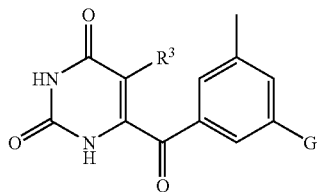

thereby forming a compound of Formula (III):

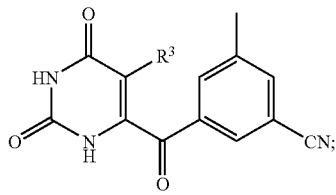

(e) reacting the compound of Formula (III) with $R^1Z^1$, wherein $Z^1$ is a leaving group, thereby forming a compound of Formula (IV):

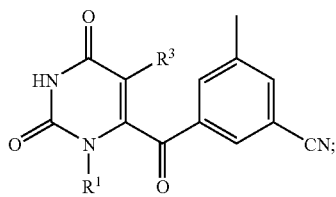

(f) reacting the compound of Formula (IV) with $Y-X^2-O-X^1-Z^2$, wherein $Z^2$ is a leaving group, thereby forming the compound of Formula (I).

2. The method of claim 1, wherein the cyanide reagent comprises a palladium(0) or palladium(II) catalyst and a cyanide ion source.

3. The method of claim 2 wherein the cyanide reagent comprises a cyanide ion source selected from the group consisting of alkali metal cyanides, alkaline earth cyanides, transition metal cyanides, CuCN, $Zn(CN)_2$, potassium hexacyanoferrate, trialkylsilylcyanide, acetone cyanohydrin, and benzylthiocyanate.

4. The method of claim 3 wherein the cyanide reagent comprises the palladium(0) or palladium(II) catalyst selected from the group consisting of $Pd_2dba_3$, $Pd(dba)_2$, $PdBr_2$, $PdCl_2$, $Pd(acetate)_2$, $Pd(trifluoroacetate)_2$, $Pd(triphenylphosphine)_4$, $PdCl_2(triphenylphosphine)_2$, $Pd(tri-tert-butylphosphine)_2$ and Pd on carbon.

5. The method of claim 4 wherein the cyanide reagent further comprises a phosphine-containing ligand selected from the group consisting of 1,1'-bis(diphenylphosphino)ferrocene (DPPF), di(1-admamantyl)-1-butylphosphine, 2-di-tert-butylphosphino-1,1'-binaphthyl, 2-(dicyclohexylphosphino)-2',6'-dimethoxy-1,1'-biphenyl (S-Phos), 2-(dicyclohexylphosphino)-2',4',6'-tri-iso-propyl-1,1'-biphenyl (X-Phos), 1,5-bis(diphenylphosphino)pentane, tri(cyclohexyl)phosphine, triphenylphosphine, and tri(butyl)phosphine.

6. The method of claim 5 wherein the cyanide reagent comprises the cyanide ion source that is $Zn(CN)_2$.

7. The method of claim 6 wherein G of Formula (II) is Br.

8. The method of claim 6, wherein each $R^1$ and $R^3$ is independently alkyl.

9. The method of claim 6, wherein Y is:

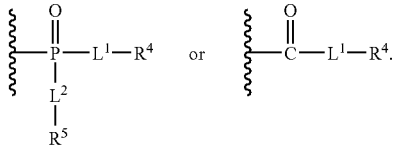

10. The method of claim 6, wherein $Y-X^2-O-X^1-Z^2$ is alkyl-C(O)-O-alkylene-$Z^2$, and $Z^2$ is Br or I.

11. The method of claim 10, wherein $Y-X^2-O-X^1-Z^2$ is $CH_3-C(O)-O-CH_2-Br$ or $CH_3-C(O)-O-CH_2-I$.

12. The method of claim 8, wherein:
$R^1$ is ethyl;
$R^3$ is isopropyl; and
$Y-X^2-O-X^1-Z^2$ is $CH_s-C(O)-O-CH_2Br$.

13. The method of claim 6, wherein $R^1Z^1$ is an alkylating agent selected from the group consisting of alkyl bromides, alkyl iodides, alkyl alkylsulfonates, alkyl arylsulfonates, alkyl triflates, alkyl carbonates, alkyl fluorosulfonates, and dialkyl sulfates.

14. The method of claim 13, wherein $R^1$ is ethyl.

15. The method of claim 1, further comprising treating the compound of Formula (III) with a metal chelating agent and an activated carbon reagent.

16. The method of claim 1, further comprising:
(c) preparing the compound of Formula (II) by hydrolyzing a compound of Formula (VI):

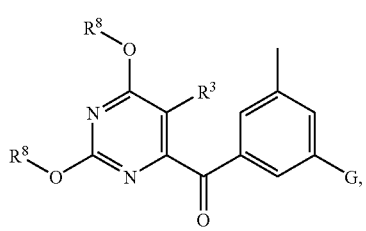

wherein G is Cl, Br, or I and each $R^8$ is a hydroxyl protecting group.

17. The method of claim 16, wherein $R^3$ is alkyl and each $R^8$ is independently alkyl or arylalkyl.

18. The method of claim 16, further comprising:
(b) preparing the compound of Formula (VI) by the oxidation of a compound of Formula (VII):

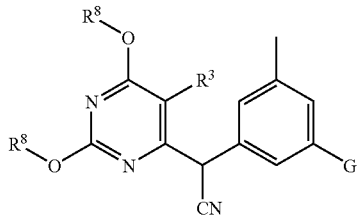
(VII)

wherein G is Cl, Br or I and each $R^8$ is a hydroxyl protecting group.

19. The method of claim 18, wherein $R^3$ is alkyl and each $R^8$ is independently alkyl or arylalkyl.

20. The method of claim 18, further comprising:
(a) reacting a compound of Formula (VIII) with 3-chloro-5-methylbenzyl cyanide, 3-bromo-5-methylbenzyl cyanide or 3-iodo-5-methylbenzyl cyanide:

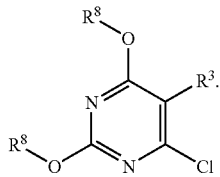
(VIII)

21. The method of claim 20, wherein $R^3$ is alkyl and each $R^8$ is independently alkyl or arylalkyl.

22. The method of claim 7 wherein:

the cyanide reagent comprises $Pd_2$ $dba_3$, DPPF or Zn$(CN)_2$;

$R^1Z^1$ is ethyl iodide;

$R^3$ is isopropyl; and

Y—$X^2$—O—$X^1$—$Z^2$ is $CH_3$—C(O)—O—$CH_2$Br.

23. The method of claim 18, wherein:

$R^1Z^1$ is ethyl iodide;

$R^3$ is isopropyl;

$R^8$ is methyl, unsubstituted benzyl, or substituted benzyl;

Y—$X^2$—O—$X^1$—$Z^2$ is $CH_3$—C(O)—O—$CH_2$Br;

G is Br;

the cyanide reagent comprises $Pd_2$ $dba_3$, DPPF and Zn$(CN)_2$; and the oxidation comprises a reaction with an alkali metal hydride and $O_2$.

* * * * *